(12) United States Patent
Sankaran et al.

(10) Patent No.: US 9,089,347 B2
(45) Date of Patent: Jul. 28, 2015

(54) MEDICAL DEVICE WITH DUAL EXPANSION MECHANISM

(75) Inventors: Meera Sankaran, Cupertino, CA (US); Derek Rothwell, Los Altos, CA (US)

(73) Assignee: ORTHOPHOENIX, LLC, Dallas, TX (US)

( * ) Notice: Subject to any disclaimer, the term of this patent is extended or adjusted under 35 U.S.C. 154(b) by 766 days.

(21) Appl. No.: 11/773,871

(22) Filed: Jul. 5, 2007

(65) Prior Publication Data

US 2008/0009875 A1    Jan. 10, 2008

Related U.S. Application Data

(60) Provisional application No. 60/818,996, filed on Jul. 7, 2006.

(51) Int. Cl.
*A61B 17/32* (2006.01)
*A61B 17/16* (2006.01)
*A61B 17/00* (2006.01)

(52) U.S. Cl.
CPC ......... *A61B 17/1671* (2013.01); *A61B 17/1617* (2013.01); *A61B 2017/00867* (2013.01); *A61B 2217/005* (2013.01)

(58) Field of Classification Search
USPC .................. 606/167, 159, 190, 192, 198, 79
See application file for complete search history.

(56) References Cited

U.S. PATENT DOCUMENTS

| | | | |
|---|---|---|---|
| 4,083,369 A | 4/1978 | Sinnreich | |
| 4,313,434 A | 2/1982 | Segal | |
| 4,327,736 A | 5/1982 | Inoue | |

(Continued)

FOREIGN PATENT DOCUMENTS

| | | |
|---|---|---|
| DE | 3922044 | 2/1991 |
| DE | 3922044.3 | 2/1991 |

(Continued)

OTHER PUBLICATIONS

Acquarulo, Jr., et al., "Enhancing Medical Device Performance with Nanocomposite Polymers." Medical Devicelink, web page at: http://www.devicelink.com/grabber.php3?URL=http://www.devicelink.com/mddi.archive/ . . . as available via the Internet and printed Jan. 17, 2005, 8 pages.

(Continued)

*Primary Examiner* — Thomas McEvoy
*Assistant Examiner* — Julie A Szpira
(74) *Attorney, Agent, or Firm* — Ascenda Law Group, PC

(57) ABSTRACT

Apparatuses and methods for accessing a tissue and expanding an apparatus within the tissue are disclosed. In one embodiment, an apparatus includes a first expandable member and a second expandable member disposed within the first expandable member. The first expandable member is configured to disrupt a body when in an expanded configuration and rotated relative to the body. The second expandable member is configured to block at least a portion of disrupted portions of the body from being disposed within the first expandable member. In some embodiments, the first expandable member is coupled to a sheath. The first expandable member is configured to be inserted at least partially into the body while disposed within a lumen of the sheath. The sheath is configured to be moved proximally while at least partially inserted into the body such that the first expandable member is moved from its collapsed to its expanded configuration.

39 Claims, 28 Drawing Sheets

(56) References Cited

U.S. PATENT DOCUMENTS

| | | |
|---|---|---|
| 4,969,888 A | 11/1990 | Scholten et al. |
| 5,108,404 A | 4/1992 | Scholten et al. |
| 5,163,949 A | 11/1992 | Bonutti |
| 5,224,945 A * | 7/1993 | Pannek, Jr. .................... 606/159 |
| 5,254,091 A | 10/1993 | Aliahmad |
| 5,258,005 A | 11/1993 | Christian |
| 5,275,610 A | 1/1994 | Eberbach |
| 5,331,975 A | 7/1994 | Bonutti |
| 5,336,178 A | 8/1994 | Kaplan et al. |
| 5,439,447 A | 8/1995 | Miraki |
| 5,460,170 A | 10/1995 | Hammerslag |
| 5,667,520 A | 9/1997 | Bonutti |
| 5,685,826 A | 11/1997 | Bonutti |
| 5,707,390 A | 1/1998 | Bonutti |
| 5,716,325 A * | 2/1998 | Bonutti ........................ 600/204 |
| 5,728,123 A | 3/1998 | Lemelson et al. |
| 5,743,851 A | 4/1998 | Moll et al. |
| 5,755,732 A | 5/1998 | Green et al. |
| 5,857,982 A | 1/1999 | Milliman et al. |
| 5,863,284 A | 1/1999 | Klein |
| 5,904,670 A | 5/1999 | Schreiner |
| 5,972,015 A | 10/1999 | Scribner et al. |
| 6,030,406 A * | 2/2000 | Davis et al. .................... 606/198 |
| 6,042,596 A | 3/2000 | Bonutti |
| 6,048,346 A | 4/2000 | Reiley et al. |
| 6,066,154 A | 5/2000 | Reiley et al. |
| 6,127,597 A | 10/2000 | Beyar et al. |
| 6,217,585 B1* | 4/2001 | Houser et al. .................. 606/108 |
| 6,235,043 B1 | 5/2001 | Reiley et al. |
| 6,238,402 B1* | 5/2001 | Sullivan et al. ............... 606/108 |
| 6,241,734 B1 | 6/2001 | Scribner et al. |
| 6,248,110 B1 | 6/2001 | Reiley et al. |
| 6,280,456 B1* | 8/2001 | Scribner et al. ............... 606/192 |
| 6,423,083 B2 | 7/2002 | Reiley et al. |
| 6,440,138 B1 | 8/2002 | Reiley et al. |
| 6,468,279 B1 | 10/2002 | Reo |
| 6,575,919 B1 | 6/2003 | Reiley et al. |
| 6,592,559 B1 | 7/2003 | Pakter et al. |
| 6,607,544 B1 | 8/2003 | Boucher et al. |
| 6,613,054 B2 | 9/2003 | Scribner et al. |
| 6,623,505 B2 | 9/2003 | Scribner et al. |
| 6,632,235 B2 | 10/2003 | Weikel et al. |
| 6,641,587 B2 | 11/2003 | Scribner et al. |
| 6,645,213 B2 | 11/2003 | Sand et al. |
| 6,663,647 B2 | 12/2003 | Reiley et al. |
| 6,676,665 B2* | 1/2004 | Foley et al. .................... 606/105 |
| 6,679,886 B2 | 1/2004 | Weikel et al. |
| 6,692,563 B2 | 2/2004 | Zimmermann |
| 6,716,216 B1 | 4/2004 | Boucher et al. |
| 6,719,761 B1 | 4/2004 | Reiley et al. |
| 6,719,773 B1 | 4/2004 | Boucher et al. |
| 6,719,803 B2 | 4/2004 | Bonutti |
| 6,726,691 B2 | 4/2004 | Osorio et al. |
| 6,746,451 B2 | 6/2004 | Middleton et al. |
| 6,780,175 B1* | 8/2004 | Sachdeva et al. ............. 604/531 |
| 6,814,736 B2 | 11/2004 | Reiley et al. |
| 6,863,672 B2 | 3/2005 | Reiley et al. |
| 6,887,246 B2 | 5/2005 | Bhatnagar et al. |
| 6,899,719 B2* | 5/2005 | Reiley et al. .................. 606/192 |
| 6,951,566 B2* | 10/2005 | Lary ............................. 606/159 |
| 6,960,215 B2 | 11/2005 | Olson, Jr. et al. |
| 6,979,341 B2 | 12/2005 | Scribner et al. |
| 7,014,633 B2 | 3/2006 | Cragg |
| 7,077,865 B2 | 7/2006 | Bao et al. |
| 7,153,307 B2 | 12/2006 | Scribner et al. |
| 7,226,481 B2 | 6/2007 | Kuslich |
| 7,311,719 B2 | 12/2007 | Bonutti |
| 7,452,351 B2 | 11/2008 | Miller et al. |
| 2001/0049531 A1 | 12/2001 | Reiley et al. |
| 2002/0026195 A1 | 2/2002 | Layne et al. |
| 2002/0026197 A1 | 2/2002 | Foley et al. |
| 2002/0161373 A1 | 10/2002 | Osorio et al. |
| 2003/0009130 A1* | 1/2003 | Stecker et al. ................ 604/104 |
| 2003/0032963 A1 | 2/2003 | Reiss et al. |
| 2003/0088249 A1 | 5/2003 | Furderer |
| 2003/0220650 A1 | 11/2003 | Major et al. |
| 2003/0229372 A1 | 12/2003 | Reiley et al. |
| 2004/0102774 A1 | 5/2004 | Trieu |
| 2004/0153064 A1 | 8/2004 | Foley et al. |
| 2004/0225296 A1 | 11/2004 | Reiss et al. |
| 2005/0033402 A1* | 2/2005 | Cully et al. .................... 623/1.11 |
| 2005/0038383 A1 | 2/2005 | Kelley et al. |
| 2005/0090852 A1* | 4/2005 | Layne et al. .................. 606/190 |
| 2005/0149022 A1 | 7/2005 | Shaolian et al. |
| 2005/0149082 A1* | 7/2005 | Yee et al. ...................... 606/159 |
| 2005/0182417 A1 | 8/2005 | Pagano |
| 2005/0209629 A1 | 9/2005 | Kerr et al. |
| 2005/0234493 A1 | 10/2005 | Carr et al. |
| 2005/0288766 A1 | 12/2005 | Plain et al. |
| 2006/0106461 A1 | 5/2006 | Embry et al. |
| 2006/0116690 A1 | 6/2006 | Pagano |
| 2006/0235417 A1 | 10/2006 | Sala |
| 2006/0271061 A1 | 11/2006 | Beyar et al. |
| 2007/0010844 A1 | 1/2007 | Gong et al. |
| 2007/0010845 A1 | 1/2007 | Gong et al. |
| 2007/0010848 A1 | 1/2007 | Leung et al. |
| 2007/0043373 A1 | 2/2007 | Sala et al. |
| 2007/0055201 A1 | 3/2007 | Seto et al. |
| 2007/0055261 A1 | 3/2007 | Reiley et al. |
| 2007/0055276 A1 | 3/2007 | Edidin |
| 2007/0060933 A1 | 3/2007 | Sankaran et al. |
| 2007/0067034 A1 | 3/2007 | Chirico et al. |
| 2007/0068329 A1 | 3/2007 | Phan et al. |
| 2007/0198013 A1 | 8/2007 | Foley et al. |
| 2007/0282443 A1 | 12/2007 | Globerman et al. |
| 2008/0077154 A1 | 3/2008 | Edwards et al. |
| 2008/0172120 A1 | 7/2008 | Fenn et al. |
| 2008/0221657 A1 | 9/2008 | Laroya et al. |

FOREIGN PATENT DOCUMENTS

| | | |
|---|---|---|
| DE | 19605615 | 8/1997 |
| EP | 1073371 B1 | 2/2001 |
| EP | 1529494 | 5/2005 |
| JP | 8038618 | 2/1996 |
| WO | WO 93/20759 | 10/1993 |
| WO | WO93/20759 | 10/1993 |
| WO | WO94/20026 | 9/1994 |
| WO | WO 94/20026 | 9/1994 |
| WO | WO96/11643 | 4/1996 |
| WO | WO 96/11643 | 4/1996 |
| WO | WO 98/22050 | 5/1998 |
| WO | 9856301 | 12/1998 |
| WO | WO 98/56301 | 12/1998 |
| WO | WO 99/51149 | 1/1999 |
| WO | WO 99/51149 | 10/1999 |
| WO | WO 00/44319 | 8/2000 |
| WO | WO 02/13700 | 2/2002 |
| WO | WO 2004/049961 | 6/2004 |
| WO | WO 2005/002454 | 1/2005 |
| WO | WO2005/027734 A3 | 3/2005 |
| WO | WO2005/048856 A1 | 6/2005 |
| WO | WO2005/110259 A1 | 11/2005 |
| WO | WO2006/037013 A1 | 4/2006 |
| WO | WO2006/042334 A3 | 4/2006 |
| WO | WO2006/088649 A1 | 8/2006 |

OTHER PUBLICATIONS

International Search Report and Written Opinion for PCT/US06/003603, dated Jun. 29, 2006, 8 pages.
International Search Report and Written Opinion for PCT/US06/026525, dated Nov. 20, 2006, 8 pages.
International Search Report and Written Opinion for PCT/US06/027049, dated Dec. 4, 2006, 7 pages.
International Searching Authority Communication for PCT/US06/026524, dated Nov. 14, 2006, 6 pages.
International Search Report and Written Opinion for PCT/US06/026524, dated Feb. 7, 2007, 17 pages.
International Search Report and Written Opinion for PCT/US07/72952, mailed on Sep. 4, 2008; 9 pages.
International Search Report and Written Opinion for PCT/US07/72952, mailed Sep. 4, 2008; 9 pages.

* cited by examiner

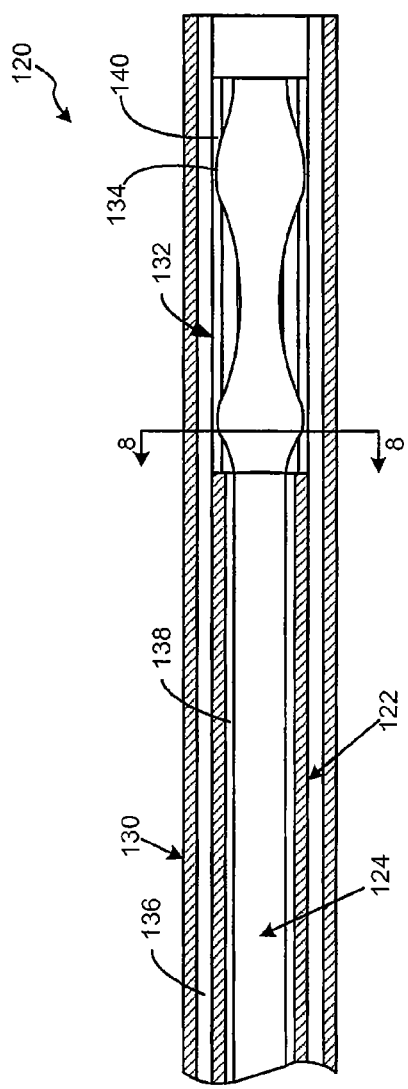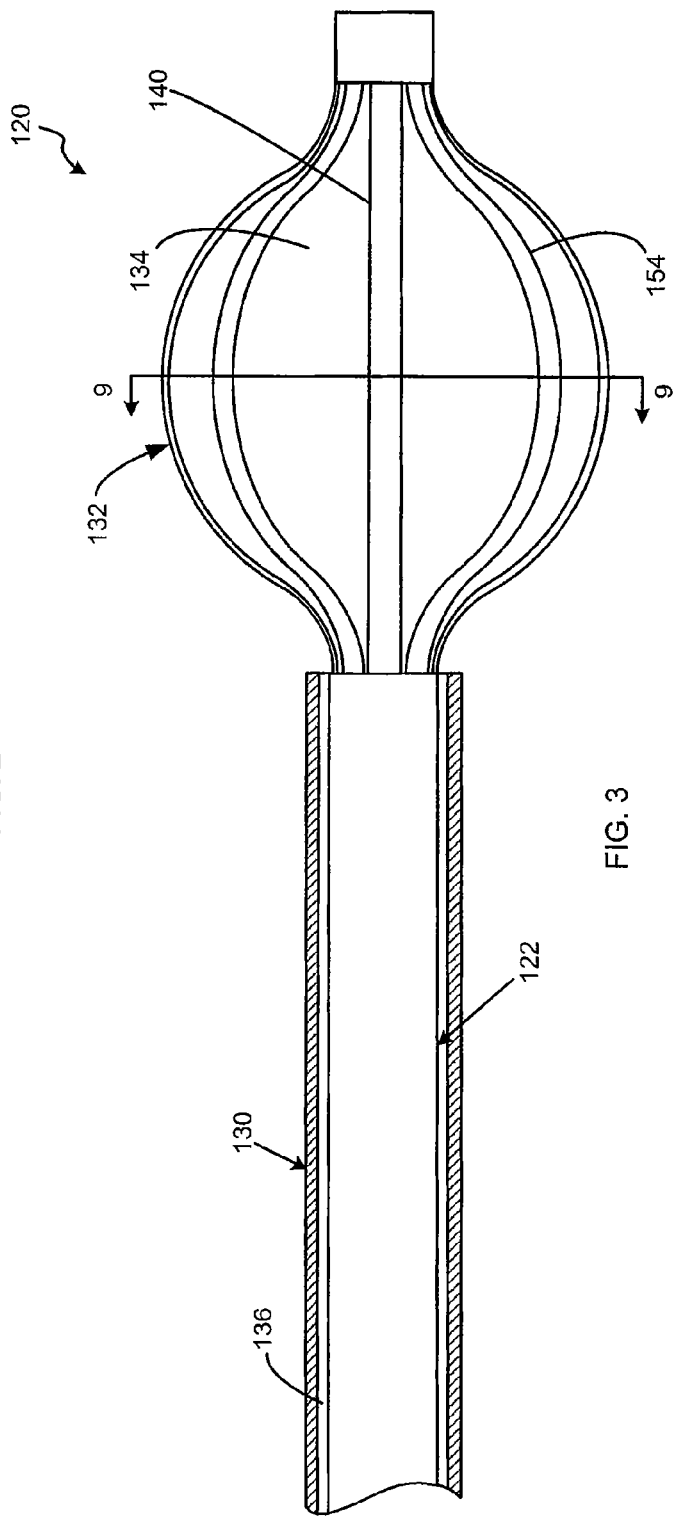
FIG. 2
FIG. 3

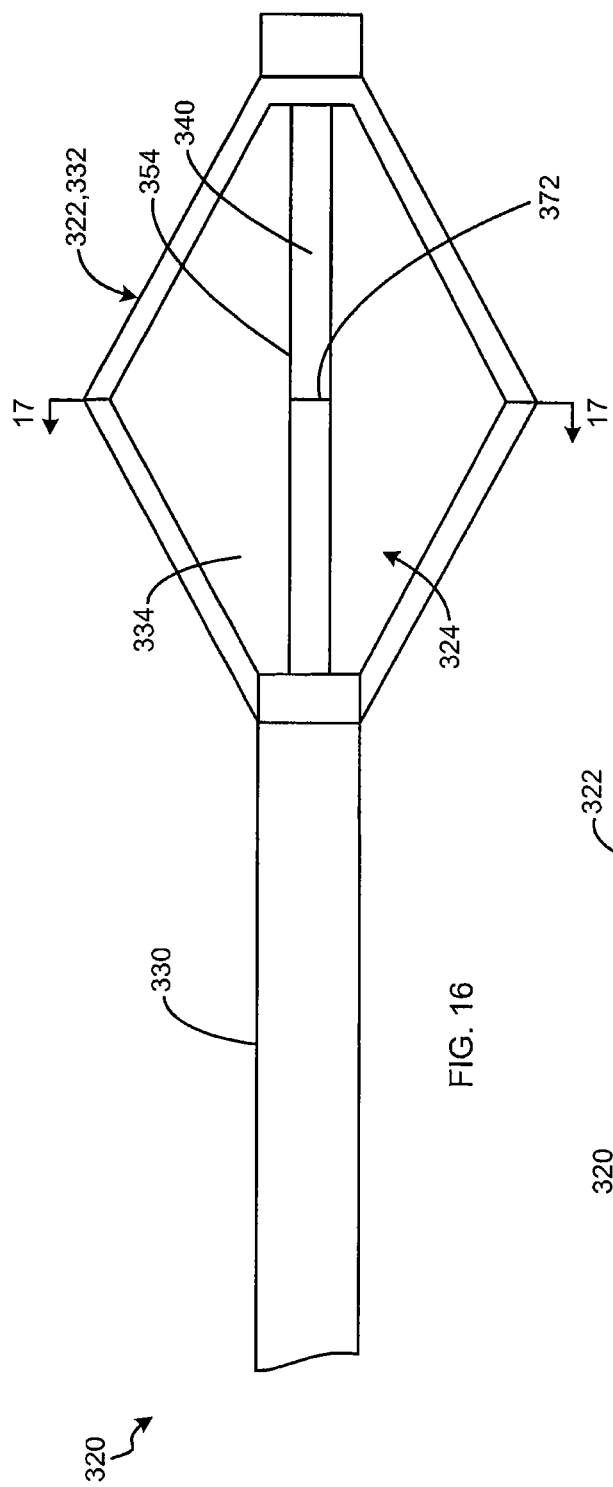
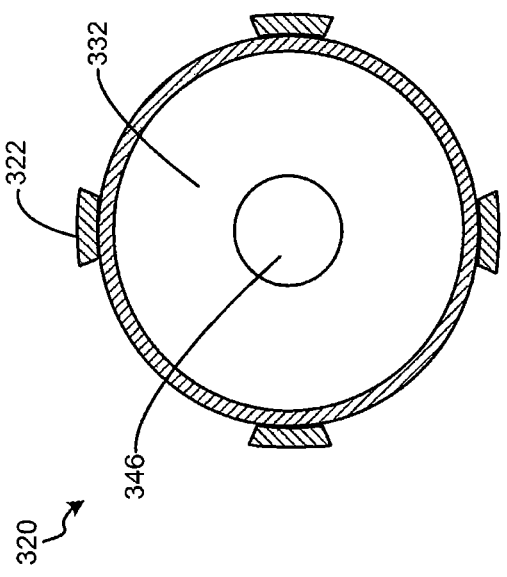
FIG. 16
FIG. 17

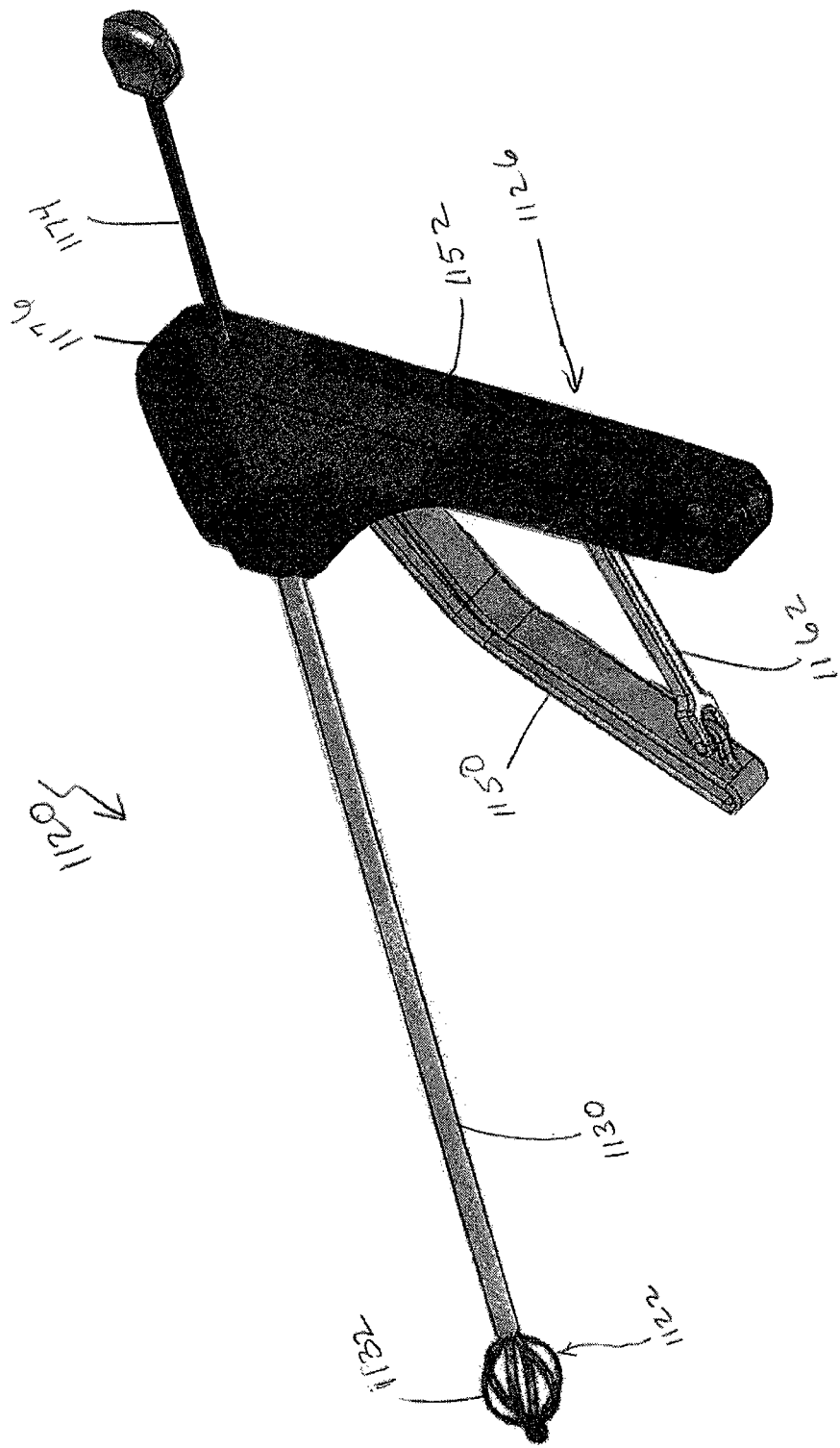

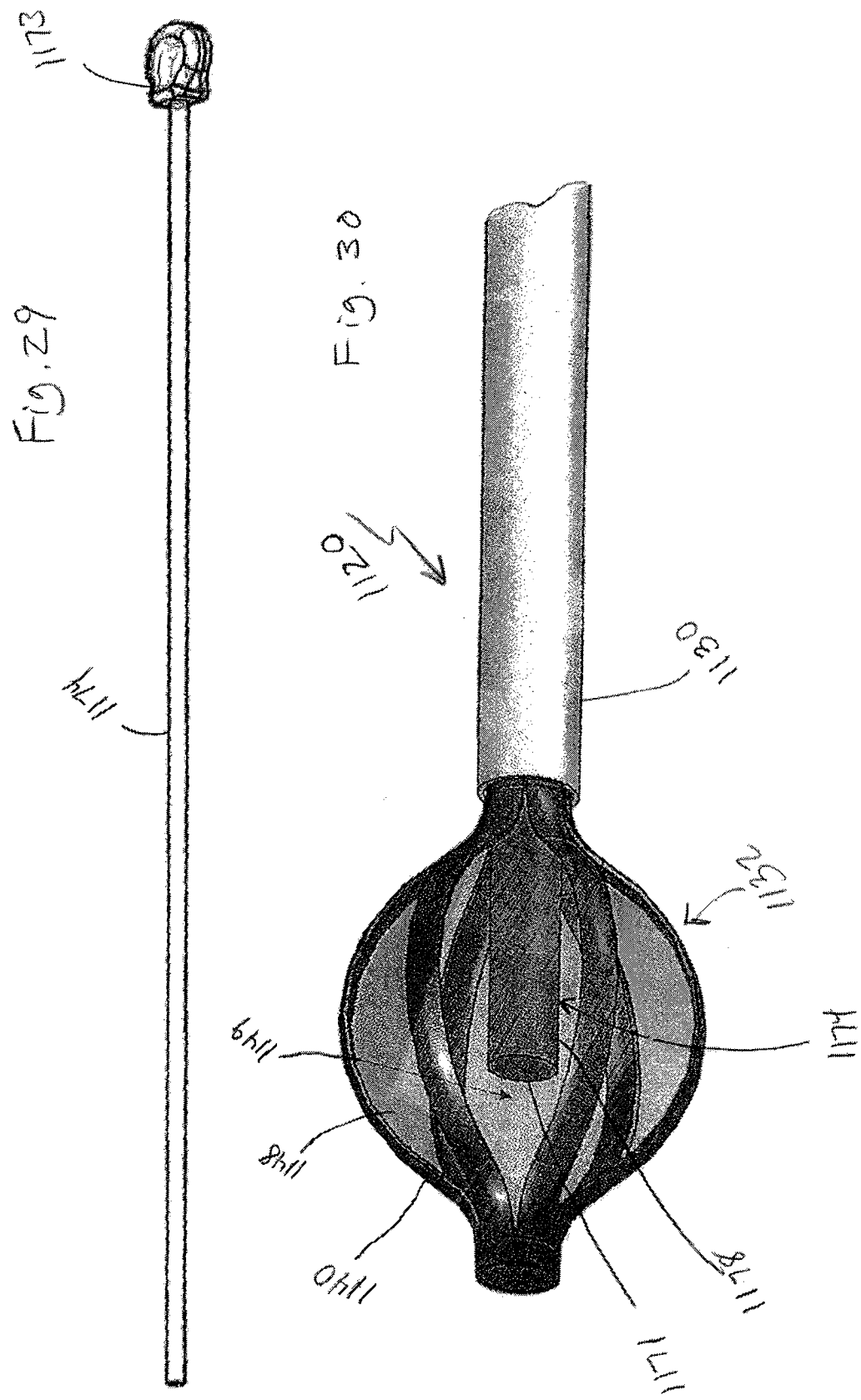

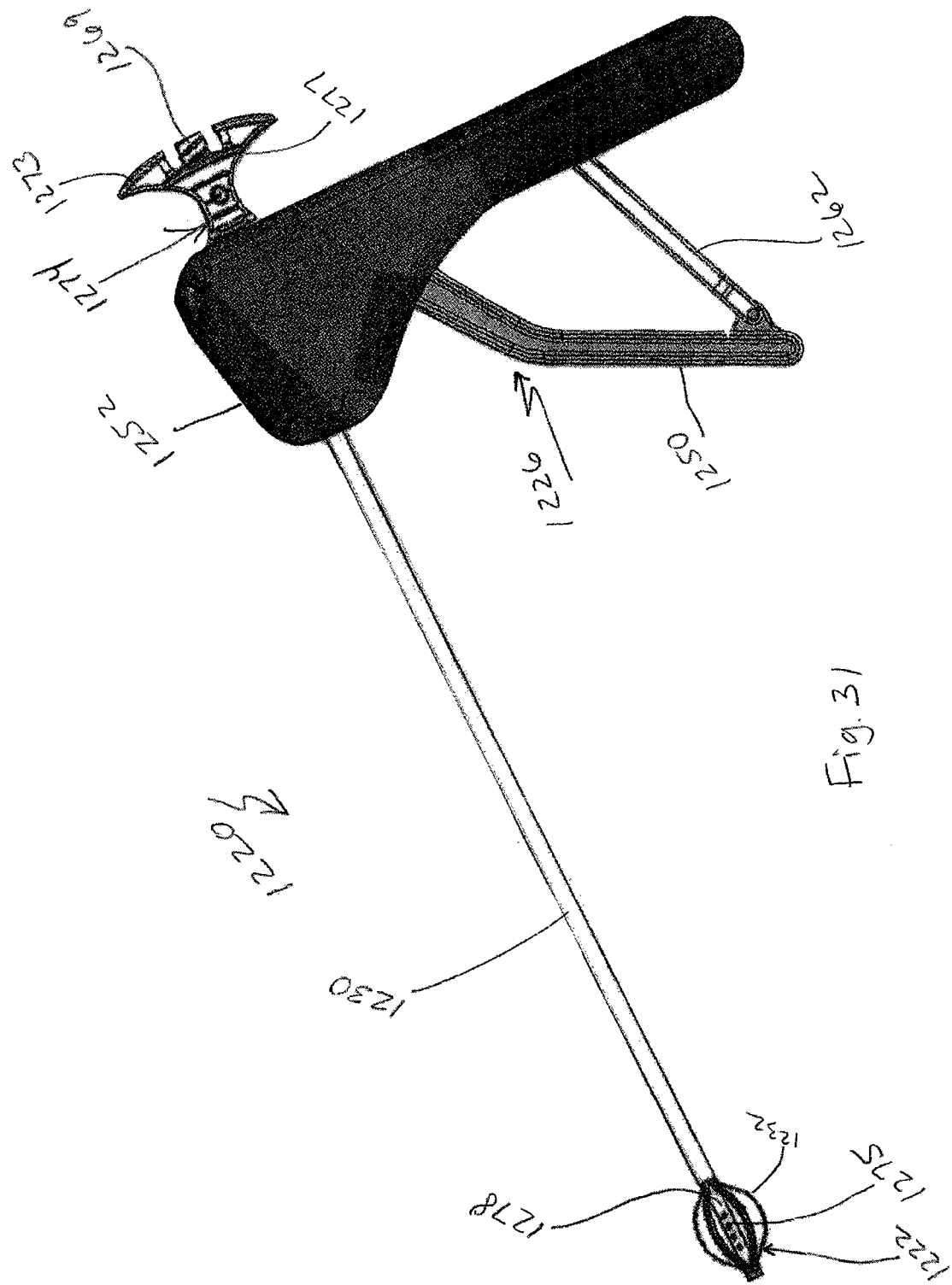

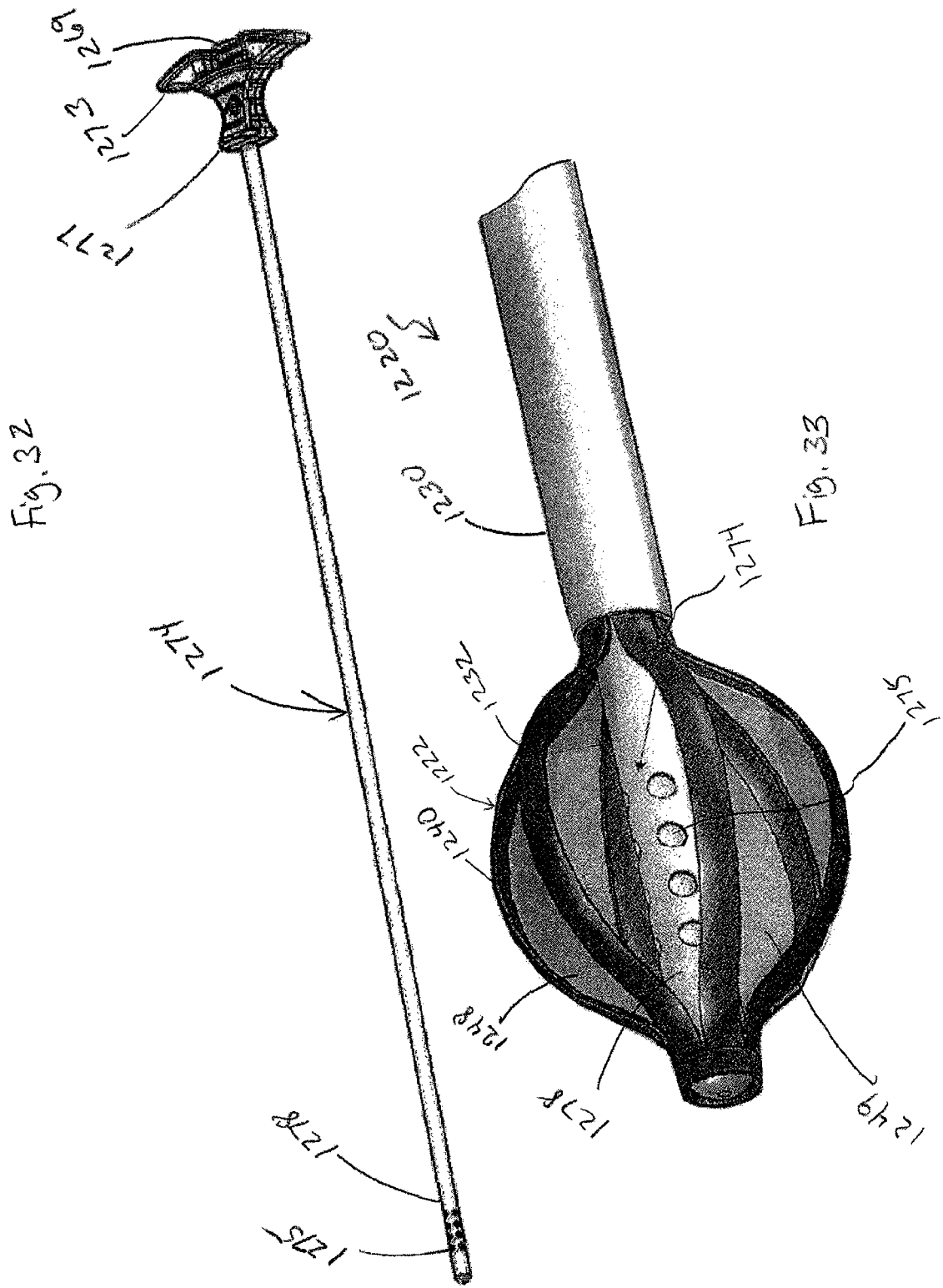

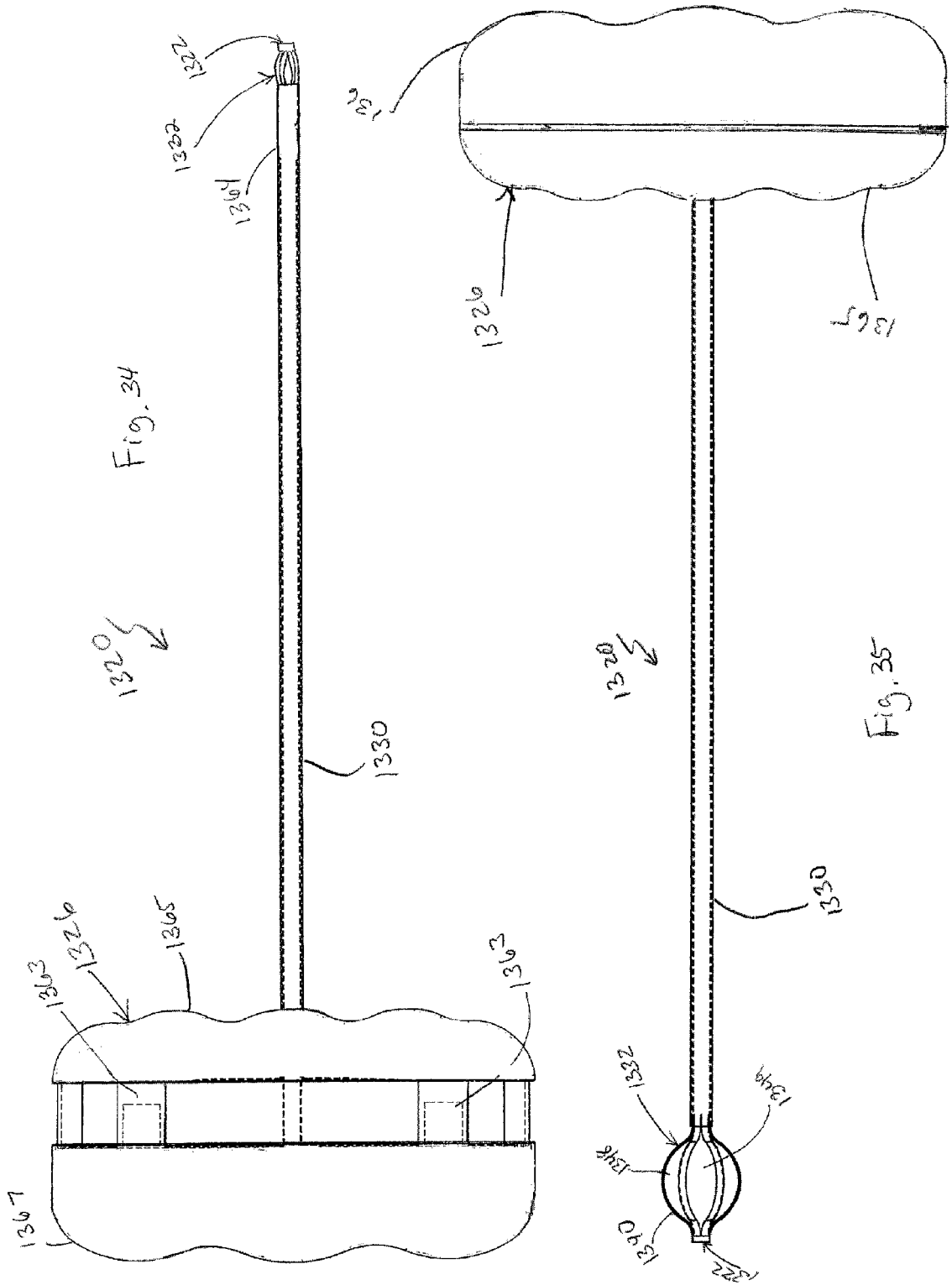

MEDICAL DEVICE WITH DUAL EXPANSION MECHANISM

CROSS-REFERENCE TO RELATED APPLICATIONS

This application claims priority to U.S. Provisional Patent Application Ser. No. 60/818,996, entitled "Medical Device With Dual Expansion Mechanism," filed Jul. 7, 2006, the entire disclosure of which is hereby incorporated by reference. This application is related to U.S. patent application Ser. No. 11/773,872, entitled "Medical Device With Expansion Mechanism," filed Jul. 5, 2007, and U.S. patent application Ser. No. 11/773,876, entitled "Medical Device With Expansion Mechanism," filed Jul. 5, 2007, both filed on same date as this application, the entire disclosures of which are hereby incorporated by reference.

BACKGROUND

The invention relates generally to medical devices and procedures, including, for example, a medical device for percutaneously accessing a tissue and expanding the device with a dual expansion mechanism.

Known medical devices are configured to access percutaneously a vertebra or other area of a spine to perform a variety of different medical procedures. Some known medical devices are configured to remove tissue from within the interior of a vertebra or intervertebral disc. Other known medical devices are configured to provide some type of cutting means to tear, disrupt and/or loosen tissue within a vertebra or intervertebral disc.

In some medical procedures, while a medical device is cutting tissue, disrupted or cut material, such as tissue within a vertebra, can become lodged within the device making it difficult to collapse the device for extraction from the vertebra.

Thus, a need exists for an apparatus and method for disrupting tissue, such tissue within a vertebra, that can be expanded and collapsed without lodging tissue in the device while in the expanded configuration.

SUMMARY OF THE INVENTION

Apparatuses and methods for accessing a tissue and expanding the apparatus within the tissue are disclosed herein. In one embodiment, an apparatus includes a first expandable member and a second expandable member disposed within the first expandable member. The first expandable member is configured to disrupt a body when ill an expanded configuration and rotated relative to the body. The second expandable member is configured to block at least a portion of disrupted portions of the body from being disposed within the first expandable member. In some embodiments, the first expandable member is coupled to a sheath. The first expandable member is configured to be inserted at least partially into the body while disposed within a lumen of the sheath. The sheath is configured to be moved proximally while at least partially inserted into the body such that the first expandable member is moved from its collapsed configuration to its expanded configuration.

BRIEF DESCRIPTION OF THE DRAWINGS

FIG. 2 is a partial cross-sectional view of a portion of a medical device shown in a collapsed configuration.

FIG. 3 is a partial cross-sectional view of a portion of the medical device of FIG. 2 shown in an expanded configuration.

FIG. 16 is a side view of a portion of a medical device according to another embodiment of the invention.

FIG. 17 is a cross-sectional view of the medical device of FIG. 16 taken along line 17-17 in FIG. 16.

FIG. 28 is a side perspective view of a medical device according to an embodiment of the invention shown in an expanded configuration.

FIG. 29 is a side perspective view of the elongate member of the medical device of FIG. 28.

FIG. 30 is a side perspective view of a distal portion of the medical device of FIG. 28 shown in an expanded configuration.

FIG. 31 is a side perspective view of a medical device according to an embodiment of the invention shown in an expanded configuration.

FIG. 32 is a side perspective view of the elongate member of the medical device of FIG. 31.

FIG. 33 is a side perspective view of a distal portion of the medical device of FIG. 31 shown in an expanded configuration.

FIG. 34 is a side view of a medical device according to an embodiment of the invention shown in a collapsed configuration.

FIG. 35 is a side view of the medical device of FIG. 34 shown in an expanded configuration.

DETAILED DESCRIPTION

Figure 1:
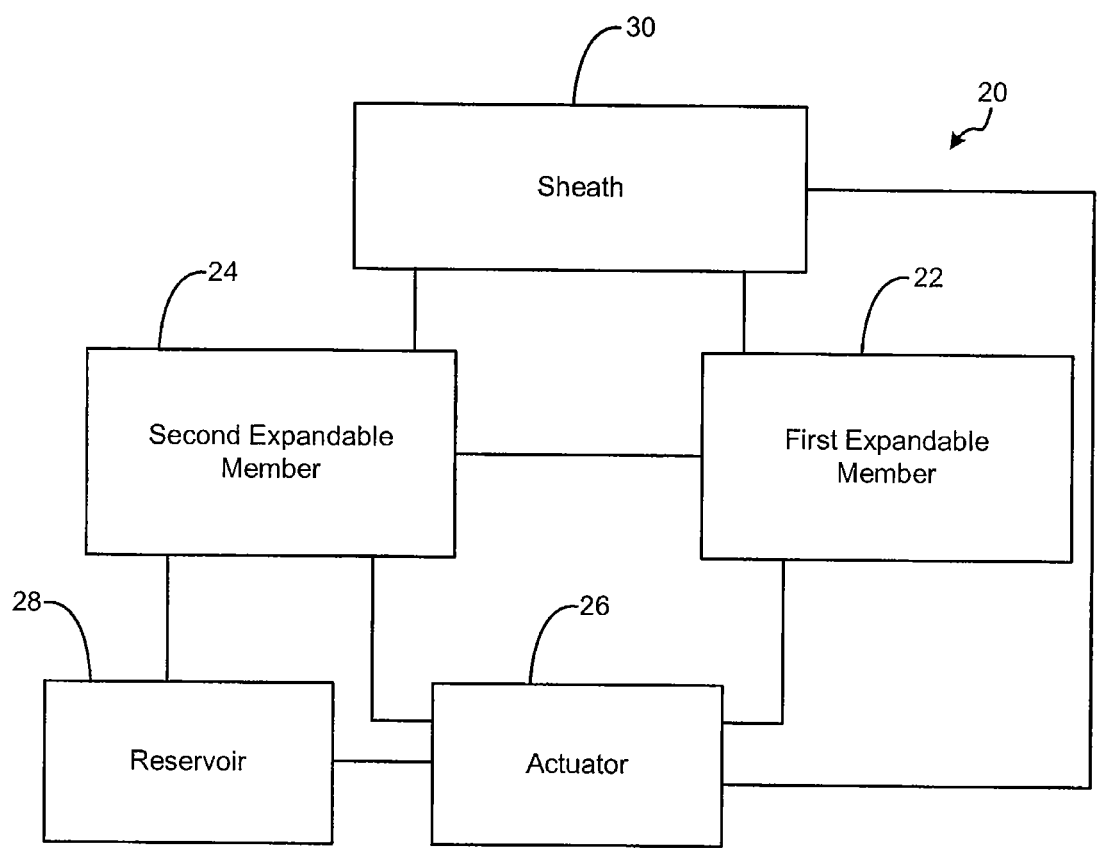
FIG. 1 is a schematic illustration of a medical device according to an embodiment of the invention.

The devices and methods described herein are configured for percutaneous deployment within an interior area of a patient's body, such as within a hard tissue area (e.g., bone structure) or soft tissue area of a patient. In some embodiments, the apparatus and methods disrupt, sever, and/or cut a portion of a tissue within a tissue area. In some embodiments, the apparatus and methods create a cavity within the tissue area. For example, a medical device according to an embodiment of the invention includes an expandable member that can be expanded while disposed within a tissue and rotated or otherwise caused to move such that a cutting portion disposed on the expanded member cuts tissue within the tissue area of the patient.

In some embodiments a medical device as described herein can be used to distract soft tissue, bone, or other biological material. For example, a medical device according to some embodiments that can be used to prepare a bone, such as a vertebral body, for insertion of an inflation balloon tamp (IBT). The medical device can be used, for example, to scrape biological material within the bone to form a cavity to allow a user to more easily insert the IBT and reduce the likelihood of ruptures to the balloon during inflation. The medical devices described herein can include a whisk-like member formed with, for example, a super-elastic Nitinol tube. The medical device can include flared portions at a distal end that are formed by laser-cut slits or notches in the sidewall of the tube. The slits or notches can be evenly spaced around a diameter of the tube, or spaced at different distances from around the tube. The flared portion can be actuated between a collapsed configuration for insertion into a body, and an expanded configuration for use in distracting, scraping, tearing, etc. biological material within a tissue or biological structure.

In some embodiments, the flared portions can be actuated using a sheath. In some embodiments, the flared portions can be actuated using a pullrod or a pushrod. In other embodiments, both a sheath and a pullrod or a pushrod can be used to actuate the flared portions. Some embodiments of a medical device include two members that have flared portions. The size of the flared portions can be varied to accommodate the formation of different sized cavities. For example, the size and/or pitch of the flared portions can be varied; the number and location of the flared portions can also be varied. In some embodiments, a medical device can have flared portions only on one side of the medical device. The medical device and flared portions can thus be sized or tailored for use in different medical procedures, and in different areas of anatomy.

In one embodiment, an apparatus includes a first expandable member configured to disrupt a body when in an expanded configuration and rotated relative to the body. A second expandable member is disposed within the first expandable member and is configured to block at least a portion of disrupted portions of the body from being disposed within the first expandable member.

In another embodiment, an elongate body includes a distal end portion having an expanded configuration and a collapsed configuration. At least a portion of a flexible member having an expanded configuration and a collapsed configuration is disposed within the distal end portion of the elongate body. A reservoir is in fluid communication with the flexible member. An actuator is coupled to the reservoir. The actuator is configured to actuate the elongate body between its collapsed configuration and its expanded configuration while simultaneously actuating movement of fluid contained within the reservoir and the flexible member to actuate the flexible member between its collapsed configuration and its expanded configuration.

In one embodiment, an apparatus includes a first elongate body having a distal end portion. The distal end portion has a plurality of cutting portions, a collapsed configuration and an expanded configuration. The plurality of cutting portions is configured to disrupt at least a portion of tissue within a biological body when the distal end portion is in the expanded configuration. A second elongate body is movably coupled to the first elongate body. An actuator is operatively coupled to a proximal end portion of the second elongate body and configured to bias the second elongate body such that the distal end portion of the first elongate body is in the expanded configuration. The actuator is configured to move the second elongate body such that first elongate body is in the collapsed configuration when the actuator is actuated.

In one embodiment, a method includes rotating a distal end portion of an expandable medical device within a biological body such that at least a portion of tissue within the biological body is disrupted. The distal end portion of the medical device defines a plurality of openings in communication with an interior region. After rotating the distal end portion of the medical device, a distal end portion of an elongate member is moved distally within a lumen of the medical device and into the interior region of the distal end portion of the medical device. The elongate member is configured to displace tissue fragments from the interior region. In some embodiments, after the rotating, a fluid is introduced into the interior region of the medical device via the elongate member.

In one embodiment, an apparatus includes a first elongate body that includes a distal end portion having a plurality of cutting portions, a collapsed configuration and an expanded configuration. The plurality of cutting portions is configured to disrupt at least a portion of tissue within a biological body when the distal end portion is in the expanded configuration. A second elongate body is movably coupled to the first elongate body. An actuator is operatively coupled to a proximal end portion of the second elongate body and configured to bias the second elongate body such that the distal end portion of the first elongate body is in the expanded configuration. The actuator is configured to move the second elongate body such that first elongate body is in the collapsed configuration when the actuator is actuated.

In one embodiment, an apparatus includes a sheath defining a lumen and an elongate body at least partially disposed within the lumen of the sheath. The elongate body has a distal end portion that has a collapsed configuration and an expanded configuration. A rod is movably disposed within a lumen of the elongate body. An actuator is coupled to the sheath and the rod and configured to bias the sheath into a first position and the rod into a first position such that the distal end portion of the elongate body is in the expanded configuration.

In one embodiment, a method includes inserting a medical device in a collapsed configuration at least partially into a biological body. The medical device has a sheath and an elongate body at least partially disposed within a lumen of the sheath. After the inserting, the sheath is moved proximally such that a distal end portion of the elongate body is disposed outside of the lumen of the sheath and within the biological body. The distal end portion of the elongate body has a plurality of cutting portions. The method also includes rotating the medical device such that the cutting portions of the distal end portion of the elongate body disrupt at least a portion of tissue within the biological body.

In one embodiment, a method includes rotating a distal end portion of an expandable medical device within a biological body such that at least a portion of tissue within the biological body is disrupted. The distal end portion of the medical device defines a plurality of openings in communication with an interior region. After the rotating, a distal end portion of an elongate member is moved distally within a lumen of the medical device and into the interior region of the distal end portion of the medical device. The elongate member is configured to displace tissue fragments from the interior region.

In one embodiment, an apparatus includes an elongate body that includes a distal end portion having a collapsed configuration and an expanded configuration. The distal end portion of the elongate body defines a plurality of openings in communication with an interior region when the distal end portion of the elongate body is in the expanded configuration. An elongate member is movably disposable within a lumen of the elongate body. The elongate member is configured to move tissue fragments from the interior region and through the plurality of openings when the distal end portion is in the expanded configuration.

It is noted that, as used in this written description and the appended claims, the singular forms "a," "an" and "the" include plural referents unless the context clearly dictates otherwise. Thus, for example, the term "a lumen" is intended to mean a single lumen or a combination of lumens. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body. Thus, for example, the catheter end inserted inside a patient's body would be the distal end of the catheter, while the catheter end outside a patient's body would be the proximal end of the catheter.

The term "tissue" is used here to mean an aggregation of similarly specialized cells that are united in the performance of a particular function. For example, a tissue can be a soft tissue area (e.g., a muscle), a hard tissue area (e.g., a bone structure), a vertebral body, an intervertebral disc, a tumor, etc. The terms "body" and "biological body" are also referred to herein to have a similar meaning as the term tissue.

The term "cutting portion" is used here to mean a component of an apparatus having at least one cutting surface and being configured to, for example, cut, sever, disrupt, scrape, or tear tissue. The cutting portion can be, for example, a cutting surface disposed on an elongate body, such as a cutting surface disposed on an edge of an expandable portion of an elongate body. The cutting portion can also be a separate component coupled to a medical device.

The term "sheath" is used here to mean a component of the apparatus having one or more passageways configured to receive a device or other component. For example, a sheath can be substantially tubular. A sheath can be a variety of different shapes and size, such as having a round, square, rectangular, triangular, elliptical, or octagonal inner and/or outer perimeter. The sheath can be, for example, a cannula.

FIG. 1 is a schematic illustration of a medical device according to an embodiment of the invention. A medical device 20 includes a first expandable member 22 and a second expandable member 24 disposed at least partially within an interior volume or region (not shown in FIG. 1) defined by the first expandable member 22. The first expandable member 22 can be for example, disposed on or incorporated with an elongate body. Likewise, the second expandable member 24 can be disposed on or incorporated with an elongate body. A first cutting portion (not shown in FIG. 1) can be disposed on the first expandable member 22, as will be described in more detail below with reference to specific embodiments. The cutting portion can be a separate component coupled to the first expandable member 22 and/or second expandable member 24, or a sharpened edge or surface defined by the first expandable member 22 and/or second expandable member 24.

In some embodiments, the first expandable member 22 can be disposed within a lumen of a third elongate body, such as a sheath 30, that can be used to move the first expandable member 22 between a collapsed configuration and an expanded configuration. For example, the first expandable member 22 can be formed with a shape-memory material, such as Nitinol (e.g., a nickel titanium alloy), and have an expanded preset configuration. The first expandable member 22 can include multiple arms and have a whisk-type shape. For example, the first expandable member 22 can be formed from a tubular member that has a portion with slits cut (e.g., laser cut) along an outer surface to define multiple arms. In some embodiments, the first expandable member 22 can be a separate component coupled to an elongate body. For example, the arms can be formed as one or more separate components that are coupled to an elongate body. The first expandable member 22 can be restrained in the collapsed configuration while disposed within a lumen of the sheath. When the first expandable member 22 is released from or disposed outside of the lumen of the sheath, the first expandable member 22 will be biased into its preset expanded configuration. Alternatively, the first expandable member 22 can be found with other material(s) such as a flexible material that will allow the first expandable member 22 to be moved to an expanded configuration with the assistance of another component, such as a balloon disposed within an interior of the first expandable member 22.

As stated above, the second expandable member 24 is at least partially disposed within an interior volume defined by the first expandable member 22. The second expandable member 24 has a collapsed configuration and an expanded configuration. The second expandable member 24 can be formed at least in part, for example, from an expandable flexible material. For example, the second expandable member 24 can include a balloon. In some embodiments, the second expandable member 24 can alternatively be formed with a shape-memory material, such as Nitinol, and include, for example, multiple expandable ribs similar to the arms described above for the first expandable member 22. For example, the second expandable member 24 can be formed with a tubular member having slits cut along an outer wall and have a whisk shape similar to the first expandable member 22.

The medical device 20 can also include an actuator 26 that can be used to actuate the first expandable member 22 and the second expandable member 24 between their respective collapsed configurations and expanded configurations. In some embodiments, for example, as stated above, the first expandable member 22 can be disposed within a lumen of the sheath 30, and the second expandable member 24 can be disposed within an interior region of the first expandable member 22. The sheath 30 can be moved or actuated by the actuator 26 between a first position and a second position. When the sheath 30 is in the first position, the first expandable member 22 and the second expandable member 24 are constrained within the lumen of the sheath 30 in their collapsed configurations. When the sheath 30 is moved to its second position, the first expandable member 22 and the second expandable member 24 are each positioned outside of the lumen of the sheath 30 such that the first expandable member 22 and the second expandable member 24 are moved to their respective expanded configurations. The actuator 26 can include a handle (not shown in FIG. 1) that can be actuated by a user to move the sheath between its first position and its second position.

In some embodiments, the actuator 26 can include an optional reservoir 28 that defines an interior region that can receive and contain a fluid therein. The reservoir 28 can be coupled to and in fluid communication with the second expandable member 24. Thus, fluid can be received and contained within a closed fluid system defined at least in part by the second expandable member 24 and the reservoir 28. For example, the reservoir 28 can be in fluid communication with the second expandable member 24 with, for example, a shaft, hose or other member (not shown in FIG. 1). In such an embodiment, a volume of the fluid contained within the closed fluid system can be moved out of the reservoir 28 while a volume of fluid will be moved into the second expandable member 24 simultaneously with actuating the movement of the sheath 30 into its second position. When the sheath 30 is moved to its second position, the first expandable member 22 is released and biased into its expanded configuration. The second expandable member 24 will receive a volume of fluid from within the closed fluid system, causing the second expandable member 24 to move to its expanded configuration. In some embodiments, the volume of fluid within the second expandable member 24 when in the expanded configuration is such that the second expandable member 24 in the expanded configuration has a slightly greater interior volume than an interior volume of the first expandable member 22.

In use, the medical device 20 can be percutaneously inserted into a biological body or tissue of a patient, such as a vertebral body, with the first expandable member 22 and the second expandable member 24 in their collapsed configurations. In some embodiments, the medical device 20 is inserted through a separate cannula used to gain access to a tissue site. The medical device 20 can be actuated, for example using a handle, to move the first expandable member 22 and the second expandable member 24 to their expanded configurations. With the first expandable member 22 and the second expandable member 24 in their expanded configurations and disposed within a tissue, the medical device 20 can be rotated such that a cutting portion on the first expandable member 22 and/or the second expandable member 24 scrapes, or otherwise cuts tissue, such as cancellous bone, at the tissue site. The second expandable member 24 can be used as a block to help prevent at least a portion of the scraped or disrupted tissue from entering into the interior region of the first expandable member 22, as will be described in more detail below. Blocking at least a portion of the disrupted tissue from being disposed within the interior region of the first expandable member 122 can assist in the collapsing and removal of the first expandable member 122. The first expandable member 22 and the second expandable member 24 can then be actuated or moved to their collapsed configurations, to allow the medical device 20 to be removed from the tissue.

In some embodiments, a medical device 20 includes only a single expandable member. In such an embodiment, the expandable member can be moved between an expanded configuration and a collapsed configuration using a sheath as described above, or with the use of a pushrod or a pullrod. In some embodiments, as sheath is used in conjunction with a pushrod or a pullrod. In some embodiments, a medical device 20 includes an elongate member (not shown in FIG. 1). The elongate member can be used to clear tissue fragments (e.g., bone fragments) out of an interior region defined by the expandable member. The elongate member can also be configured to introduce fluid into the interior region and/or provide suction to remove tissue fragments from within the interior region of the expandable member.

Having described above various general examples, several examples of specific embodiments are now described. These embodiments are only examples, and many other configurations of a medical device 20 are contemplated.

Figure 4:
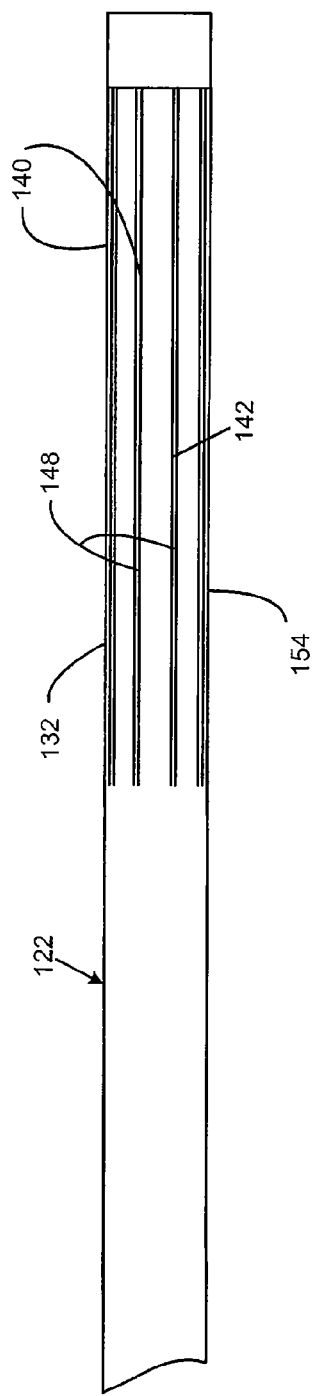
FIG. 4 is a side view of a portion of an expandable member of the medical device of FIGS. 2 and 3 shown in a collapsed configuration.
Figure 5:
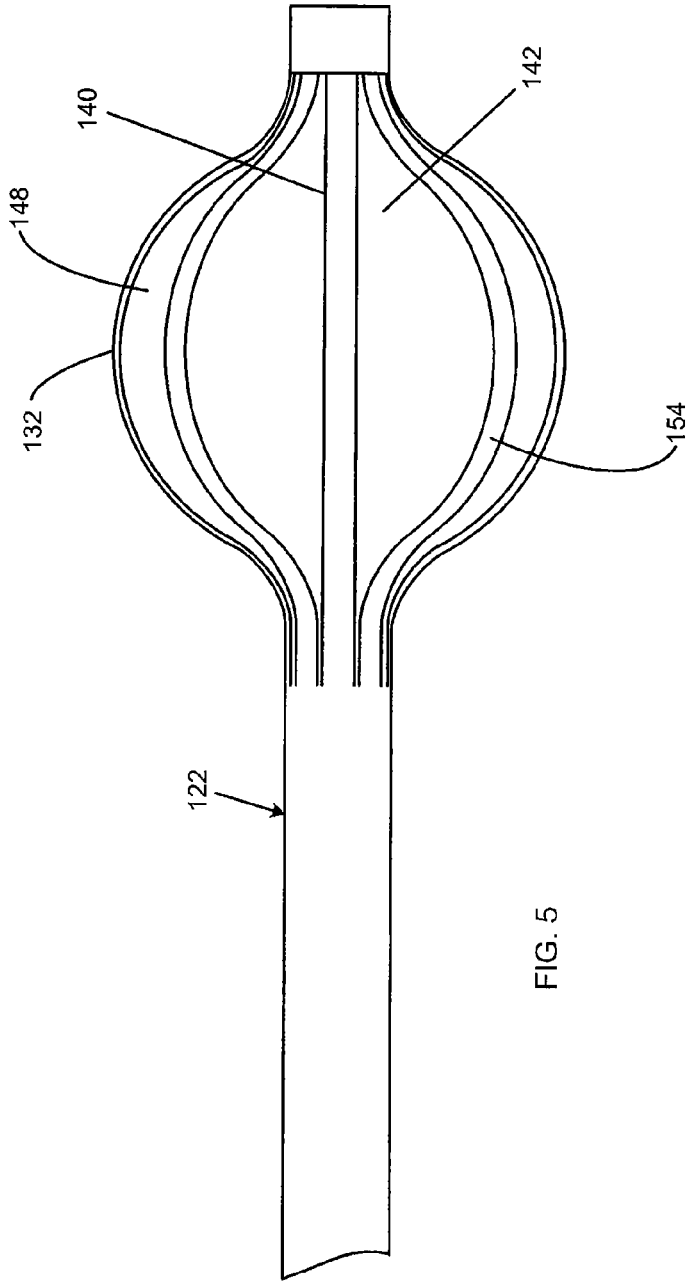
FIG. 5 is a side view of the portion of an expandable member of FIG. 4 shown in an expanded configuration.
Figure 6:
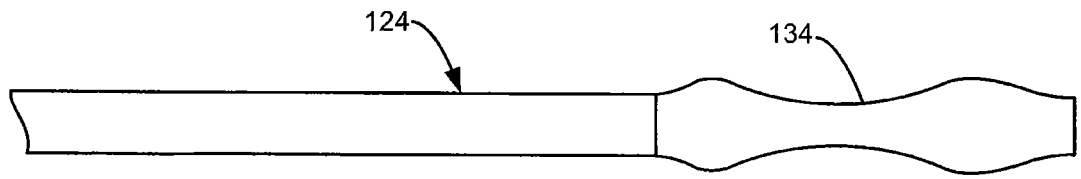
FIG. 6 is a side view of a portion of an expandable member of the medical device of FIGS. 2 and 3 shown in a collapsed configuration.
Figure 7:
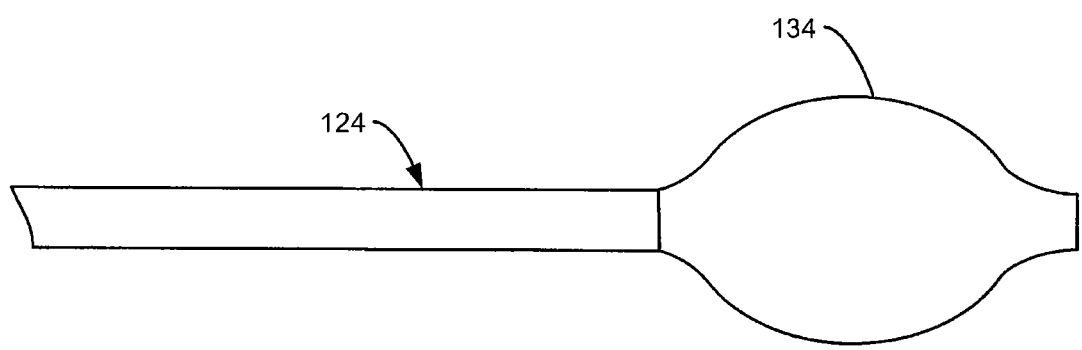
FIG. 7 is a side view of the portion of an expandable member of FIG. 6 shown in an expanded configuration.

FIGS. 2-11 illustrate a medical device according to an embodiment of the invention. As shown in FIG. 2, a medical device 120 includes a first elongate body 122 disposed within a lumen 136 of a sheath 130, and a second elongate body 124 disposed at least partially within a lumen 138 of the first elongate body 122. The second elongate body 124 also defines a lumen 146 (shown in FIGS. 8 and 9). FIG. 2 and 3 are each a side view of a portion of the medical device 120 showing the sheath 130 in cross-section and the first elongate body 122 in partial cross-section. The first elongate body 122 has a collapsed configuration, as shown in FIGS. 2 and 4, and an expanded configuration as shown in FIGS. 3 and 5. The second elongate body 124 has a collapsed configuration, as shown in FIGS. 2 and 6 and an expanded configuration as shown in FIGS. 3 and 7. In this embodiment, the first elongate body 122 has an expandable member disposed at a distal end portion 132 that includes multiple arms 140 that define openings 148 therebetween. The first elongate body 122 also includes cutting portions 154 disposed on the arms 140 of the first elongate body 122. The second elongate body 124 is a flexible member that has an expandable member, such as a flexible membrane at a distal end portion 134. For example, the flexible membrane can be a balloon. The distal end portion 134 is at least partially disposed within the distal end portion 132 of the first elongate body 122.

Figure 8:
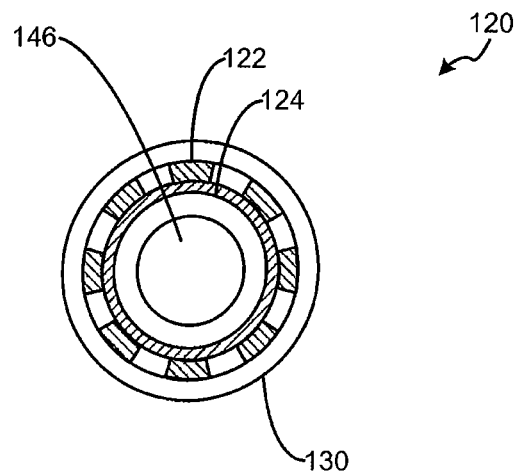
FIG. 8 is a cross-sectional view of the portion of the medical device of FIG. 2 taken along line 8-8 in FIG. 2.

The first elongate body 122 defines an interior region or volume 142 that is larger when the first elongate body 122 is in the expanded configuration (FIGS. 3, 5 and 9) than when it is in the collapsed configuration (FIGS. 2, 4 and 8). The first elongate body 122 can be formed, for example, from a tubular member that has slits cut (e.g., laser cut) in a wall of the distal end portion 132 to form the arms 140. The first elongate body 122 is also formed with a shape memory material, such as Nitinol, such that the distal end portion 132 is biased to the expanded configuration.

Figure 9:
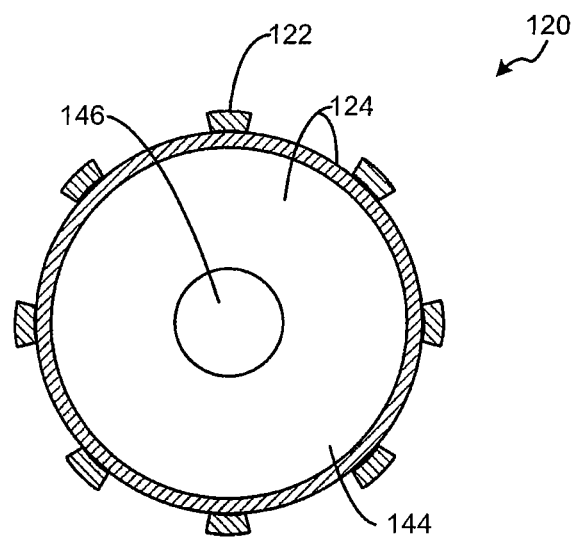
FIG. 9 is a is a cross-sectional view of the portion of the medical device of FIG. 3 taken along line 9-9 in FIG. 3.

The distal end portion 134 of the second elongate body 124 also defines an interior region 144, as best shown in the cross-sectional view of FIG. 9, that is larger when the second elongate body 124 is in the expanded configuration than when in the collapsed configuration. As stated above, in this embodiment, the distal end portion 134 of the second elongate body 124 is a flexible member, such as a balloon. In some embodiments, the second elongate body 124 is monolithically formed. In alternative embodiments, different portions of the second elongate body 124 are formed with different materials. For example, in some embodiments, the second elongate body 124 is formed entirely with a flexible material. In another alternative embodiment, the distal end portion 134 is formed with a flexible material and the remaining portion of the second elongate body 124 is formed with a non-flexible material.

As shown in FIGS. 2, 3, 9 and 10, the distal end portion 134 of the second elongate body 124 is disposed within the distal end portion 132 of the first elongate body 122. In some embodiments, the distal end portion 134 of the second elongate body 124 can be formed such that the second elongate body 124 expands to a slightly larger size than the interior region 142 of the first elongate body 122 and the distal end portion 134 of the second elongate body 124 expands partially into the openings 148 defined by the arms 140.

Figure 10:
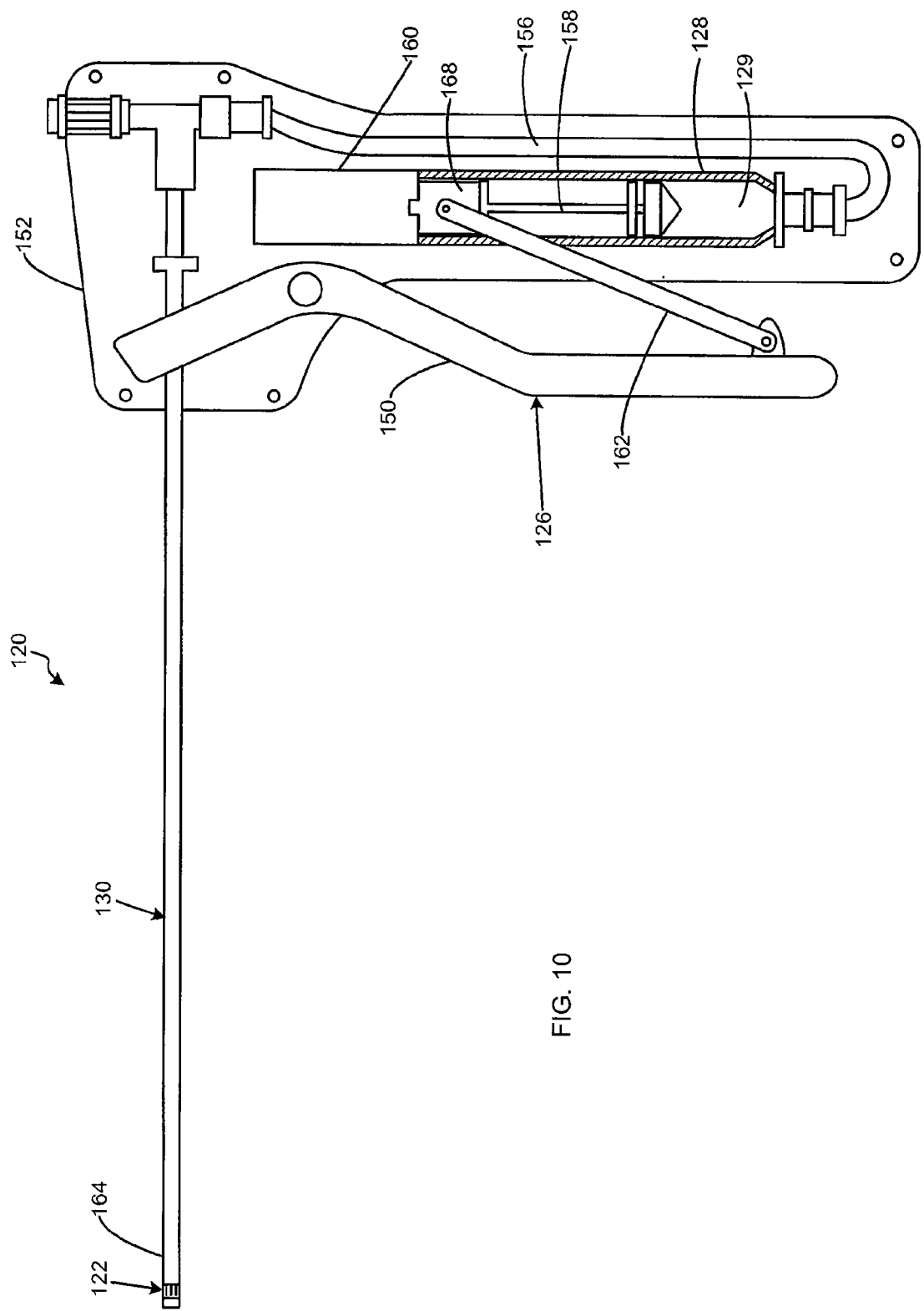
FIG. 10 is a side view of a medical device including a cut-away view of the handle according to an embodiment of the invention shown in a collapsed configuration.
Figure 11:
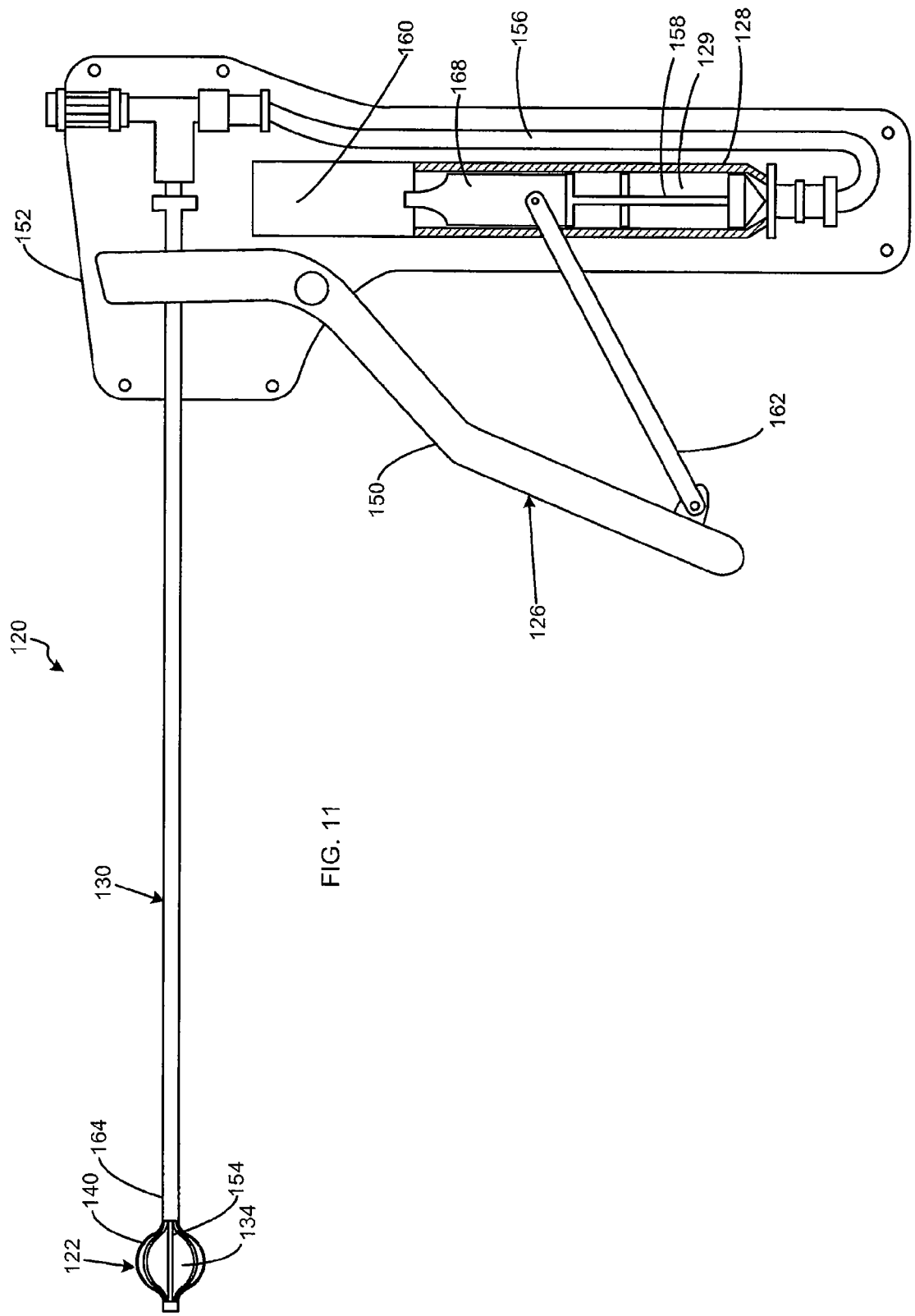
FIG. 11 is a side view of the medical device of FIG. 10 shown in an expanded configuration.

The medical device 120 also includes an actuator 126 as shown in FIGS. 10 and 11. The actuator 126 includes a handle 150 that can be actuated by a user and a housing 152. FIGS. 10 and 11 show the medical device 120 with a portion of the housing 152 removed so that a portion of an interior of the medical device 120 can be viewed. FIG. 10 illustrates the medical device 120 in a collapsed configuration and FIG. 11 illustrates the medical device 120 in an expanded configuration. The handle 150 is operatively coupled to the sheath 130 and also to a reservoir 128 and a slide member 168. The reservoir 128 defines an interior region 129. The reservoir 128 can receive and contain a fluid within the interior region 129, and is in fluid communication with the second elongate body 124 through a shaft 156 and through the lumen 146 of the second elongate body 124. In some embodiments, the shaft 156 is formed integrally with the second elongate body 124. In some embodiments, the shaft is disposed at least partially outside of the housing 150. Thus, the second elongate body 124, the reservoir 128, and the shaft 156 define a closed fluid system as will be described in more detail below. A plunger 158, such as a medical syringe plunger, is disposed within the reservoir 128. The plunger 158 and the slide member 168 are coupled to a spring (not shown), such as a compression spring, disposed within a compartment 160. The plunger 158 is also coupled to the handle 150 via a pivot arm 162. The spring biases the handle 150 into an open position as shown in FIG. 11.

To move the medical device 120 from the expanded configuration to the collapsed configuration, the user grips the handle 150 of the actuator 126 such that the handle 150 is moved toward the housing 152 as shown in FIG. 10. This action will move the sheath 130 distally to a first position in which a distal end 164 of the sheath 130 is positioned substantially over the distal end portion 132 of the first elongate body 122 (e.g., the distal end portion 132 is disposed at least partially within the lumen 136 of the sheath 130). This action will collapse the distal end portion 132 of the first elongate body 122. Simultaneously, the plunger 128 will be moved toward the spring compartment 160 and at least partially compress the spring. A volume of fluid in the distal end portion 134 of the second elongate body 124 will be drawn out of the distal end portion 134 and a volume of fluid will be drawn into the reservoir 128. In other words, a portion of the fluid within the closed fluid system will be caused to move to the reservoir 128. The fluid movement out of the distal end portion 134 allows the distal end portion 132 of the first elongate body 122 to collapse over the distal end portion 134 of the second elongate body 124. Thus, in the collapsed configuration, a volume of fluid within the distal end portion 134 of the second elongate body 124 is less than a volume of fluid in the distal end portion 134 when the second elongate body 124 is in the expanded configuration. A volume of fluid within the reservoir 128 when the distal end portion 134 of the second elongate body 124 is in the collapsed configuration is greater than a volume of fluid in the reservoir 128 when the distal end portion 134 of the second elongate body 124 is in the expanded configuration.

In the collapsed configuration, the medical device 120 can be inserted into a tissue of a patient, such as a vertebral body. For example, the medical device 120 can be inserted through an access cannula (not shown) while the user holds the handle 150 against the housing 152 as shown in FIG. 10. While disposed within the tissue, the user can release the handle 150, which will allow the spring to bias the handle 150 back to the open position, as shown in FIG. 11. This action will move the distal end 164 of the sheath 130 proximally such that the first elongate body 122 is disposed outside the lumen 136 of the sheath 130 as shown in FIG. 11. When the distal end portion 132 of the first elongate body 122 is no longer constrained by the sheath 130, the distal end portion 132 will be automatically biased to the expanded configuration. Simultaneously, the plunger 128 will move away from the spring compartment 160 (e.g., due to the biasing force of the spring) and force fluid out of the reservoir 128 and into the shaft 156. With the distal end portion 132 of the first elongate body 122 in the expanded configuration, the distal end portion 134 of the second elongate body 124 can receive a volume of fluid that has been pushed out of the reservoir 128 and move to its expanded configuration.

In the expanded configuration, the medical device 120 can be rotated or otherwise moved within the tissue such that the cutting portions 154 disposed at the distal end portion 132 of the first elongate body 122 scrape, tear, or otherwise disrupt tissue, such as cancellous bone, within the tissue. The distal end portion 134 of the second elongate body 122 will block at least a portion of the scraped, torn or disrupted tissue from entering into the interior region 142 of the first elongate body 122.

To move the medical device 120 back to the collapsed configuration, the user again grips the handle 150, such that the handle 150 is moved closer to the housing 152, as shown in FIG. 10. This will again move the medical device 120 to the collapsed configuration as described above. The user can then remove the medical device 120 from the tissue, for example, through an access cannula.

Although the first elongate body 122 has been described as being formed with a shape-memory material having a preset expanded configuration, in alternative embodiments, the first elongate body 122 can be formed with other materials that do not have shape-memory characteristics. In such an embodiment, the first elongate body 122 can be moved to its expanded configuration by actuation of the second elongate body 124 to its expanded configuration. For example, the second elongate body 124 can be moved to an expanded configuration as fluid is received within the interior region of the second elongate body 124 as described above. As this occurs, the expansion of the second elongate body 124 will also cause the first elongate body 122 to expand. To collapse the first elongate body 122, the handle 150 can be gripped by the user as described above, which will move the sheath 130 distally over the distal end portion 132 of the first elongate body 122 and collapse the distal end portion 132 of the first elongate body 122. In one variation, the first elongate body 122 can be formed with a shape-memory material and biased into a collapsed configuration. In this embodiment, when the second elongate body 124 is collapsed, the first elongate body 122 will be biased back to its collapsed configuration without the use of a sheath.

Although the actuation of the medical device 120 has been described as gripping the handle 150 to move the medical device 120 to the collapsed configuration, and releasing the handle 150 to move the medical device 120 to the expanded configuration, in alternative embodiments, the handle 150 can be actuated in an opposite manner. For example, a medical device can be configured such that the user can grip the handle against the housing to move the medical device to the expanded configuration and release the handle to move the medical device to the collapsed configuration. In other alternative embodiments, the handle can be actuated with linear movement. For example, the handle can extend parallel to an axis defined by the first elongate body and/or the second elongate body such that rather than gripping the handle against the housing to actuate the medical device, the user actuates the handle with linear motion similar to movement of a syringe.

In yet another embodiment, the medical device 120 can be actuated using a reservoir that is in fluid communication with the second elongate body through an elongate shaft. In such an embodiment, the reservoir and second elongate body can define a closed fluid system as described above where a volume of fluid is moved into the distal end portion of the second elongate body to move the distal end portion to an expanded configuration and drawn out of the distal end portion to move the distal end portion to a collapsed configuration. In this embodiment, to actuate the second elongate body from a collapsed configuration to an expanded configuration, a user can squeeze the reservoir such that a volume of fluid is pushed out of the reservoir and a volume of fluid is moved into the distal end portion of the second expandable member.

In such an embodiment, the distal end portion of the first elongate body can be formed with a shape-memory material and biased into a collapsed configuration. When the distal end portion of the second elongate body is moved to its expanded configuration, the first elongate body will also be moved to its expanded configuration by the inflation of the second expandable member. When the reservoir is released, a volume of fluid will be drawn back into the reservoir and a volume of fluid will be drawn out the distal end portion of the second elongate body, collapsing the distal end portion of the second elongate body. With the distal end portion of the second elongate body collapsed, the first elongate body will be biased back to its collapsed configuration.

Figure 12:
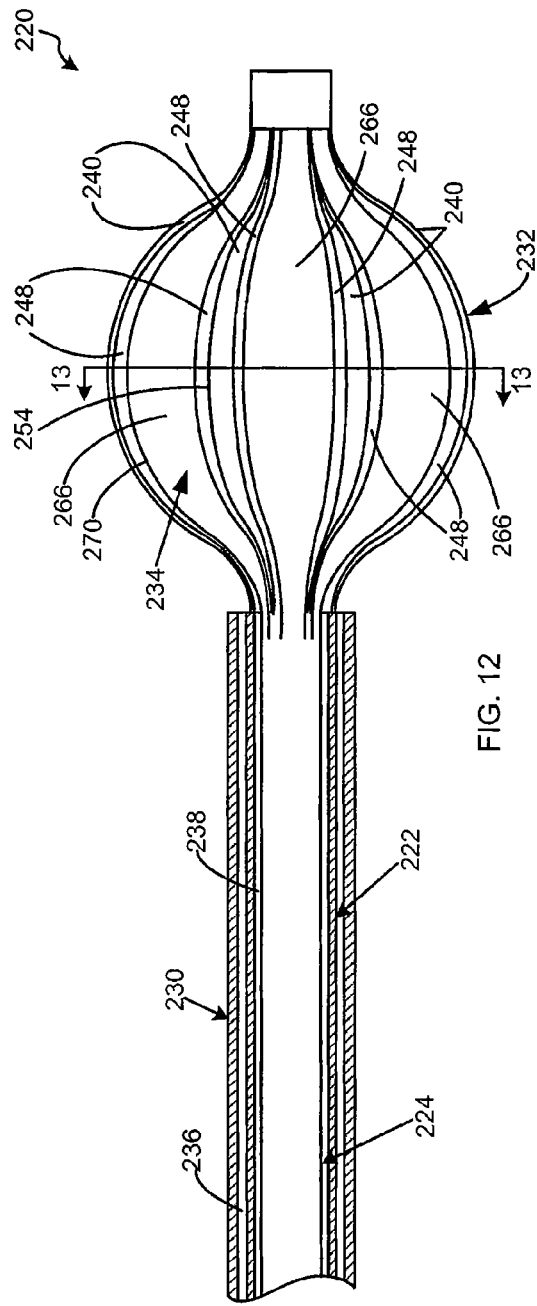
FIG. 12 is a side view shown partially in cross-section of a portion of a medical device shown in an expanded configuration.
Figure 13:
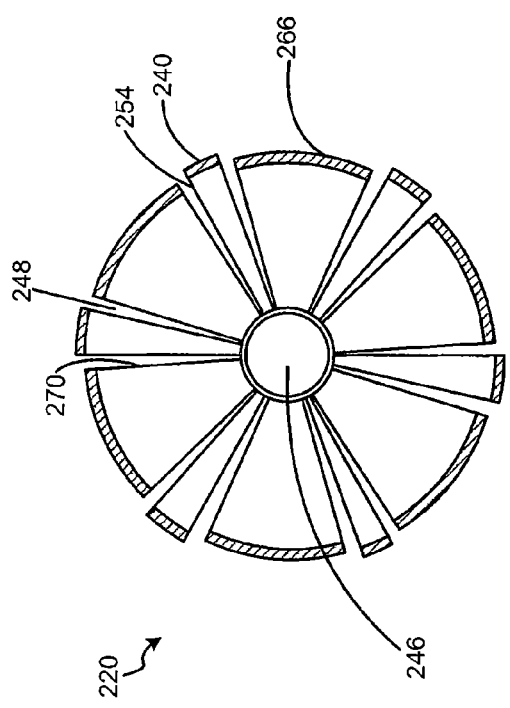
FIG. 13 is a cross-sectional view of the medical device of FIG. 12 taken along line 13-13 in FIG. 12.

FIGS. 12-15 illustrate a medical device according to another embodiment. A medical device 220 includes a first elongate body 222 disposed within a lumen 236 of a sheath 230, and a second elongate body 224 disposed at least partially within a lumen 238 of the first elongate body 222. The second elongate body 224 also defines a lumen 246 (shown in FIG. 13). FIGS. 12 and 13 are side views of a portion of the medical device 220 showing the sheath 230 in cross-section and the first elongate body 222 in partial cross-section. The first elongate body 222 has a collapsed configuration (not shown) and an expanded configuration as shown in FIGS. 12 and 13. The second elongate body 224 has a collapsed configuration (not shown) and an expanded configuration as shown in FIGS. 12 and 13.

In this embodiment, the first elongate body 222 has a distal end portion 232 that includes multiple arms 240 that define openings 248 therebetween. The first elongate body 222 also includes cutting portions 254 disposed on the arms 240 of the first elongate body 222. The second elongate body 224 has a distal end portion 234 that defines multiple ribs 266 and is at least partially disposed within the distal end portion 232 of the first elongate body 222 such that the ribs 266 are in an offset relationship with the arms 240. The second elongate body 224 also includes cutting portions 270 disposed on the ribs 266. In alternative embodiments, the second elongate body 224 does not include cutting portions.

As with the previous embodiment, the first elongate body 222 defines an interior region or volume (not shown) that is larger when the first elongate body 222 is in the expanded configuration than when it is in the collapsed configuration. The first elongate body 222 can be formed in the same manner as described in the previous embodiment, for example, from a tubular member that has slits cut in the distal end portion 232 to form the arms 240. The first elongate body 222 is also formed with a shape memory material, such as Nitinol, such that the distal end portion 232 is biased to assume the expanded configuration.

The distal end portion 234 of the second elongate body 224 also defines an interior region (not shown) that is larger when the second elongate body 224 is in the expanded configuration than when in the collapsed configuration. In this embodiment, the second elongate body 224 is formed with a shape-memory material such that the distal end portion 234 has a preset expanded configuration. For example, the distal end portion 234 of the second elongate body 224 can be formed with slits cut along an outer wall to define the ribs 266. As shown in FIGS. 12 and 13, the distal end portion 234 of the second elongate body 224 is disposed within the distal end portion 232 of the first elongate body 222 such that the ribs 266 are disposed substantially within the openings 248 defined by the arms 240.

Figure 14:
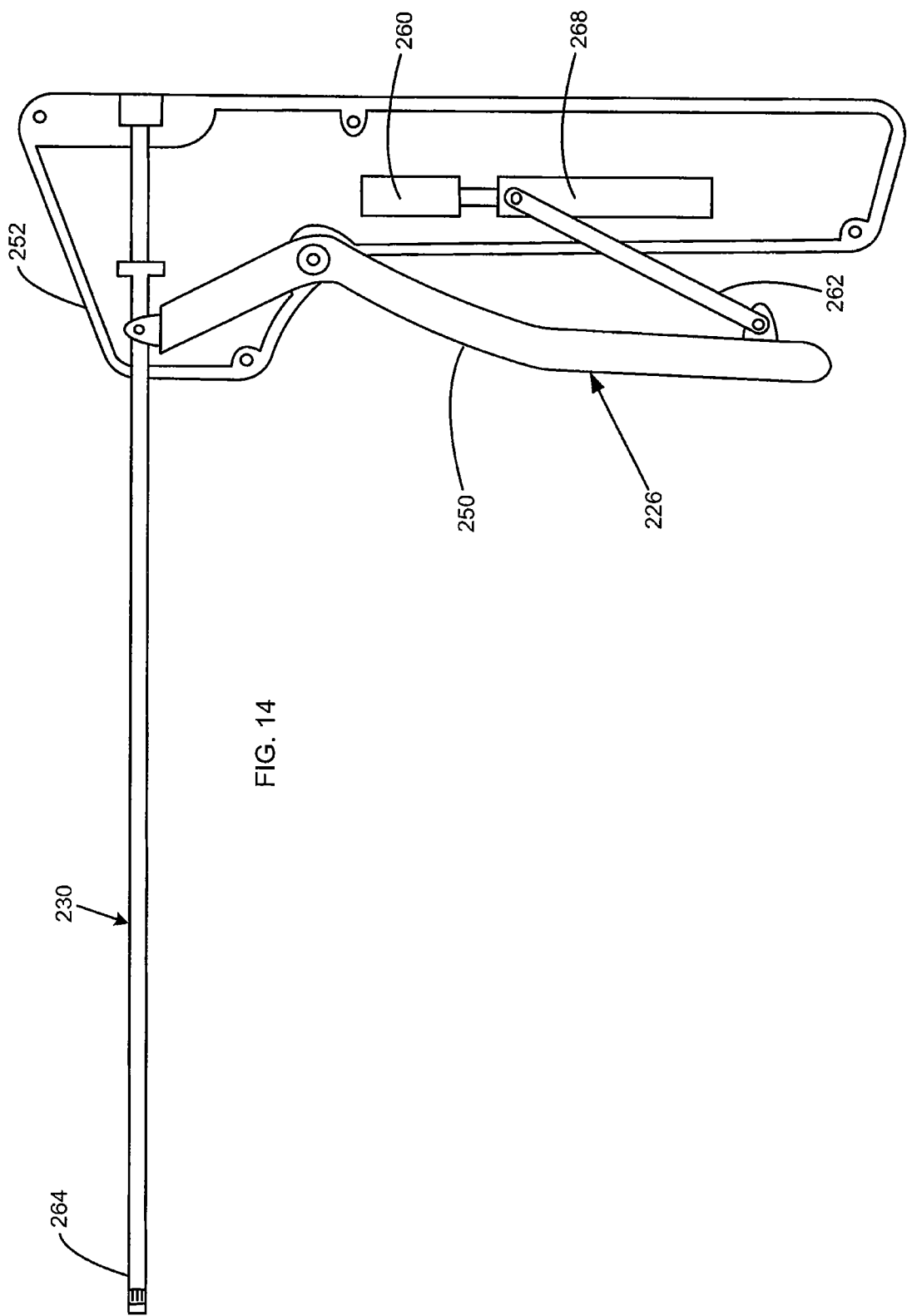
FIG. 14 is a side view of the medical device of FIG. 12 including a cut-away view of the handle shown in a collapsed configuration.
Figure 15:
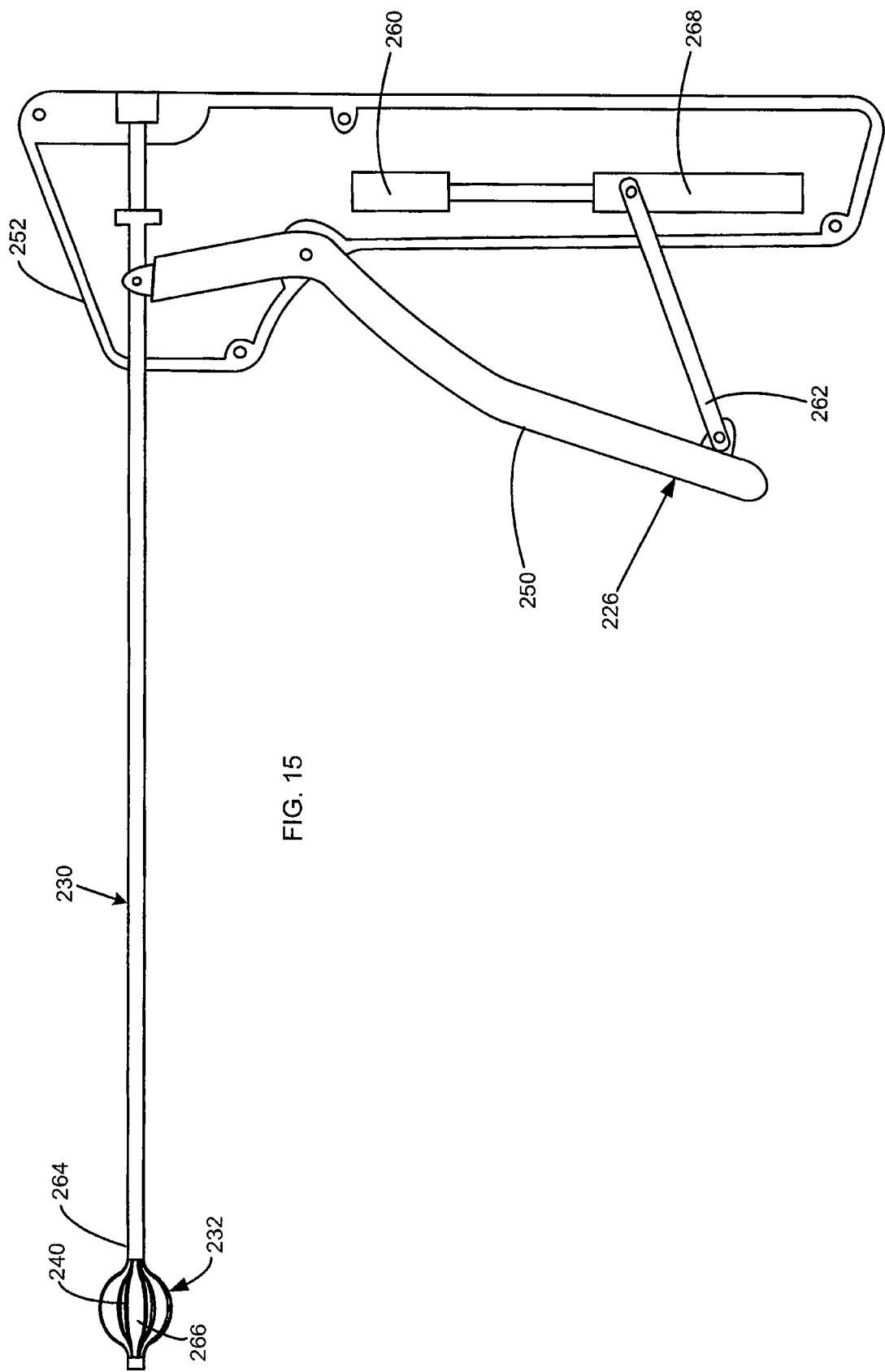
FIG. 15 is a side view of the medical device of FIG. 14 shown in an expanded configuration.

The medical device 220 also includes an actuator 226 as shown in FIGS. 14 and 15. The actuator 226 includes a handle 250 that can be actuated by a user and a housing 252. FIGS. 14 and 15 show the medical device 220 with a portion of the housing 252 removed so that a portion of an interior of the medical device 220 can be viewed. FIG. 14 illustrates the medical device 220 in a collapsed configuration; FIG. 15 illustrates the medical device 220 in an expanded configuration. In this embodiment, the handle 250 is operatively coupled to the sheath 230 as described in the previous embodiment, and also to a slide member 268 via the pivot arm 262. The slide member 268 is coupled to a spring (not shown), such as a compression spring, that is disposed within a compartment 260. As with the previous embodiment, the spring biases the handle 250 to an open position as shown in FIG. 15.

To move the medical device 220 from the expanded configuration to the collapsed configuration, the user grips the handle 250 such that the handle 250 is moved toward the housing 252 as shown in FIG. 14. This action will move the sheath 230 distally to a first position in which a distal end 264 of the sheath 230 is positioned substantially over the distal end portion 232 of the first elongate body 222. Thus, the distal end portion 232 of the first elongate body 222 and the distal end portion 234 of the second elongate body 224 will be constrained in their respective collapsed configurations within the lumen 236 of the sheath 230.

In the collapsed configuration, the medical device 220 can be inserted into a tissue of a patient, such as a vertebral body. For example, the medical device 220 can be inserted through an access cannula. While disposed within the tissue, the user can release the handle 250 to move the medical device 220 to the expanded configuration. With the handle 250 released, the spring will bias the handle 250 to the open position as shown in FIG. 15. This action will move the distal end 264 of the sheath 230 proximally such that the distal end portion 232 of the first elongate body 222 (and the distal end portion 234 of the second elongate body 224 disposed within the first elongate body 222) is disposed outside the lumen 236 of the sheath 230, as shown in FIG. 15. When the distal end portion 232 of the first elongate body 222, and the distal end portion 234 of the second elongate body 224 are no longer constrained by the sheath 230, the distal end portion 232 and the distal end portion 234 will be automatically biased to their respective expanded configurations.

In the expanded configuration, the medical device 220 can be rotated or otherwise moved within the tissue such that the cutting portions 254 of the first elongate body 222 and the cutting portions 270 of the second elongate body 224 scrape, tear, or otherwise disrupt tissue, such as cancellous bone, within the tissue. Because the ribs 266 of the distal end portion 234 of the second elongate body 222 are disposed in an offset relationship with the arms 240 (i.e., disposed within the openings 248) the ribs 266 will block at least a portion of the torn or disrupted tissue from entering into the interior region of the first elongate body 222.

To move the medical device 220 back to the collapsed configuration, the user again grips the handle 250, such that the handle 250 is moved closer to the housing 252, as shown in FIG. 14. This will again move the medical device 220 to the collapsed configuration as described above. The user can then remove the medical device 220 from the tissue, for example, through an access cannula.

FIGS. 16 and 17 illustrate yet another embodiment of a medical device. A medical device 320 is constructed similar to the medical device 120. For example, the medical device 320 includes a sheath 330, a first elongate body 322 disposed within a lumen (not shown) of the sheath 330, and a second elongate body 324 disposed within a lumen (not shown) of the first elongate body 322. In this embodiment, the first elongate body 322 includes a distal end portion 332 having multiple arms 340 and cutting portions 354 disposed on the arms 340. In this embodiment, rather than being formed from a tubular member, the arms 340 can be formed as one or more separate components, for example, with a flexible shape-memory material, such as Nitinol, and coupled to the first elongate body 322.

The second elongate body 324 includes a flexible membrane at a distal end portion 334 that is disposed within the distal end portion 332 of the first elongate body 322. The second elongate body 324 also defines a lumen 346 as shown in FIG. 17. The lumen 346 can be used to communicate fluid between the distal end portion 334 of the second elongate body 324 and a reservoir (not shown) as previously described.

In this embodiment, the distal end portion 332 is biased into an expanded configuration and includes four arms 340 that each include a hinge or break point 372. The break points 372 fold when the first elongate body 324 is moved from a collapsed configuration to the expanded configuration. The medical device 320 can be moved between an expanded configuration and a collapsed configuration in a similar manner as described above for medical device 120.

In another alternative embodiment, a medical device can include a pull-rod to actuate the expansion of a first elongate body. In such an embodiment, a sheath would not be necessary. A pull-rod can be operatively coupled to the actuator such that the first elongate body can be actuated simultaneously with the actuation of the second elongate body. For example, in an embodiment with a second elongate body having a flexible member (e.g. balloon) disposed within a first elongate body having a whisk-type configuration, the flexible member can be configured with a passageway to receive the pull-rod therethrough. The pull-rod can be pulled proximally to move the first elongate body to the expanded configuration simultaneously with the inflation of fluid within the flexible member of the first elongate body. In an embodiment with a second elongate body having a whisk-type configuration instead of a balloon, the pull-rod can be configured to actuate simultaneously both the first elongate body and the second elongate body.

In yet another embodiment, a medical device can include a second elongate body having a flexible membrane disposed within a whisk-type first elongate body. In this embodiment, the arms of the first elongate body are fixed to the flexible membrane. In such an embodiment, the sheath would not be necessary to actuate the first elongate body. For example, as the flexible membrane is inflated with fluid and moved to its expanded configuration as described above, the first elongate body would also be moved to its expanded configuration. To move the device to the collapsed configuration, the fluid can be withdrawn from the flexible membrane as described previously. As the fluid is evacuated from the flexible membrane, the first elongate body will also be drawn to its collapse d configuration.

Figure 18:
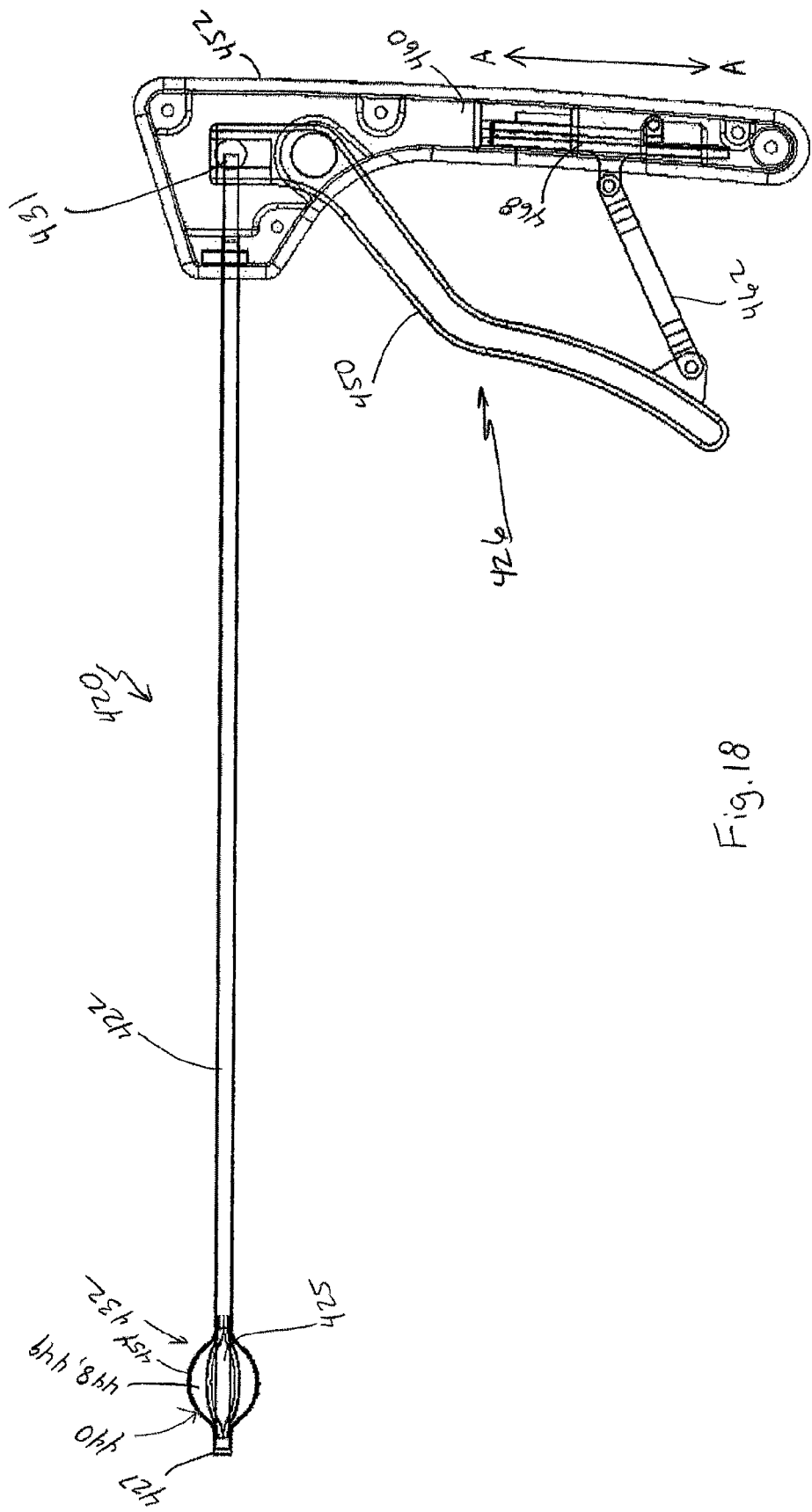
FIG. 18 is a side view of a medical device according to an embodiment of the invention shown in an expanded configuration.
Figure 19:
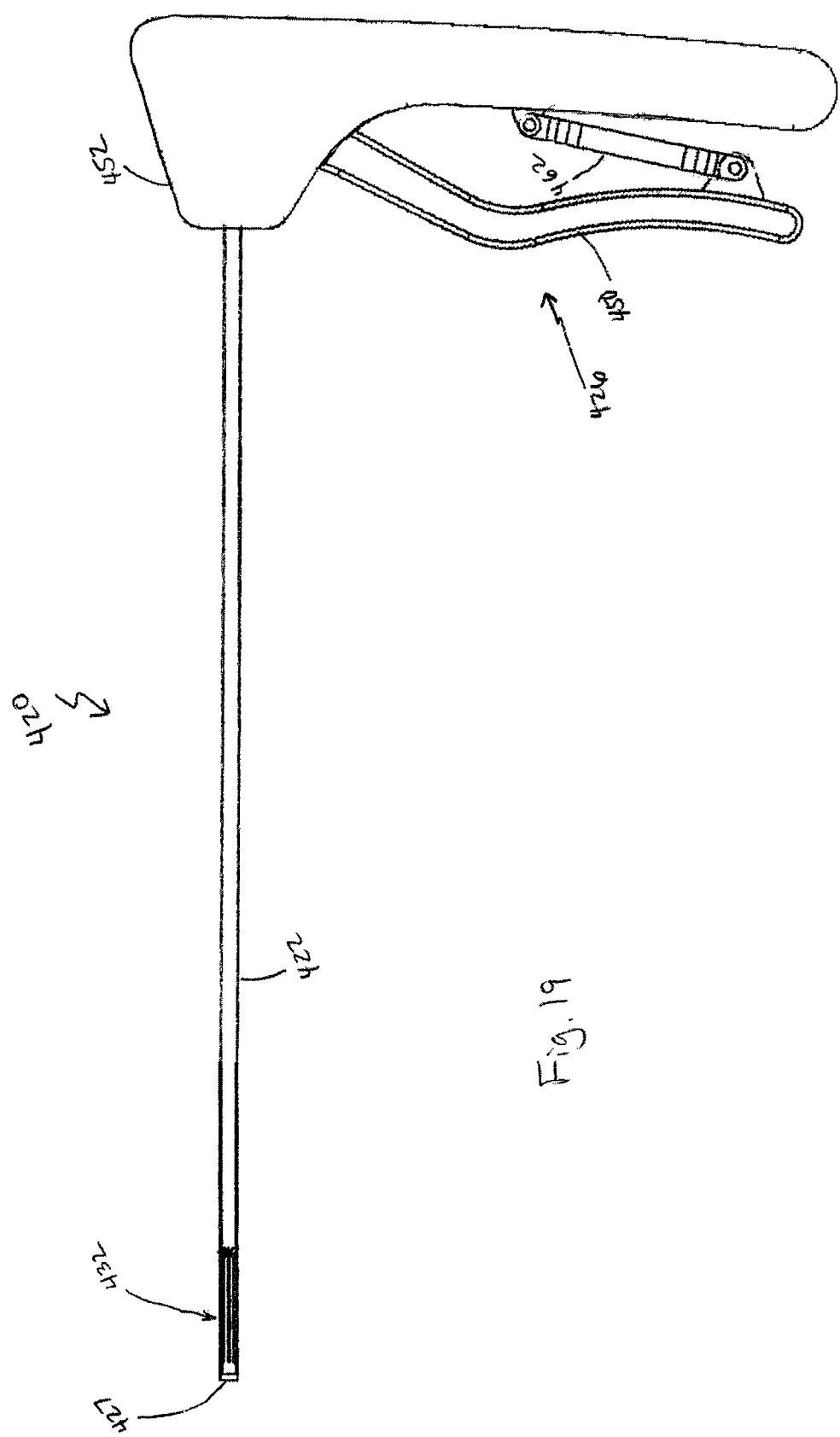
FIG. 19 is a side view of the medical device of FIG. 18 shown in a collapsed configuration.

FIGS. 18 and 19 illustrate an embodiment of a medical device using a pushrod to actuate the medical device between a collapsed configuration and an expanded configuration. In this embodiment, a medical device 420 includes an elongate body 422 movable between a collapsed configuration as shown in FIG. 19, and an expanded configuration as shown in FIG. 18. The elongate body 422 defines a lumen (not shown) and has a distal end portion 432 that includes multiple arms 440 that define openings 448 therebetween. An edge of the arms 440 define cutting portions 454. The medical device 420 also includes a rod 425 that is at least partially disposed within the lumen of the elongate body 422. A distal end of the rod 425 is coupled to a distal end 427 of the elongate body 422.

As with the previous embodiment, the elongate body 422 can be formed with a shape-memory material, such as Nitinol, and configured such that the distal end portion 432 of the elongate body 422 is biased into the expanded configuration as shown in FIG. 18. The elongate body 422 can be formed in the same manner as described in the previous embodiment, for example, from a tubular member that has slits or windows cut in the distal end portion 432 to form the arms 440. When the elongate body 422 is in the expanded configuration, the arms 440 define an interior region or volume 449 that is larger than when the elongate body 422 is in the collapsed configuration.

The rod 425 is coupled at a proximal end 431 to an actuator 426. The actuator 426 includes a handle 450 and a housing 452. FIG. 18 shows the medical device 420 with a portion of the housing 452 removed so that a portion of an interior of the medical device 420 can be viewed. In this embodiment, the handle 450 is operatively coupled to the rod 425, which is used to move the elongate body 422 between its expanded and collapsed configurations. The handle 450 is coupled to a slide member 468 via a pivot arm 462. The slide member 468 is also coupled to a spring (not shown), such as a compression spring, that is disposed within a compartment 460. The slide member 468 can move or translate back-and-forth in the direction of arrows A-A as the spring moves between a biased position and a compressed position. As with the previous embodiment, the spring biases the handle 450 to an open position as shown in FIG. 18 when the spring is in its biased position. When the handle 450 is in the open position, the rod 425 will be moved proximally to a position as shown in FIG. 18. This will at least partially collapse the distal end portion 432 (e.g., the arms 440) of the elongate body 422.

To move the elongate body 422 from the expanded configuration to the collapsed configuration, the user grips the handle 450 such that the handle 450 is moved toward the housing 452, as shown in FIG. 19. This action will compress the spring, and move the rod 425 distally, which in turn will extend or collapse the distal end portion 432 (e.g., arms 440) of the elongate body 422.

In the collapsed configuration, the medical device 420 can be inserted into a tissue of a patient, such as a vertebral body. For example, a user can grip the handle 450, as described above, and insert the medical device 420 through an access cannula and to a desired location within a tissue. While disposed within the tissue, the user can release the handle 450 to move the medical device 420 to the expanded configuration. With the handle 450 released, the spring will bias the handle 450 to the open position as shown in FIG. 18 and move the rod 425 proximally such that the distal end portion 432 of the elongate body 422 is moved to the expanded configuration. In the expanded configuration, the medical device 420 can be rotated or otherwise moved within the tissue such that the cutting portions 454 of the arms 440 scrape, tear, or otherwise disrupt tissue, such as cancellous bone, within the tissue.

To move the medical device 420 back to the collapsed configuration, the user again grips the handle 450, such that the handle 450 is moved closer to the housing 452, as shown in FIG. 19. This will again move the medical device 420 to the collapsed configuration as described above. The user can then remove the medical device 420 from the tissue, for example, through an access cannula.

Figure 20:
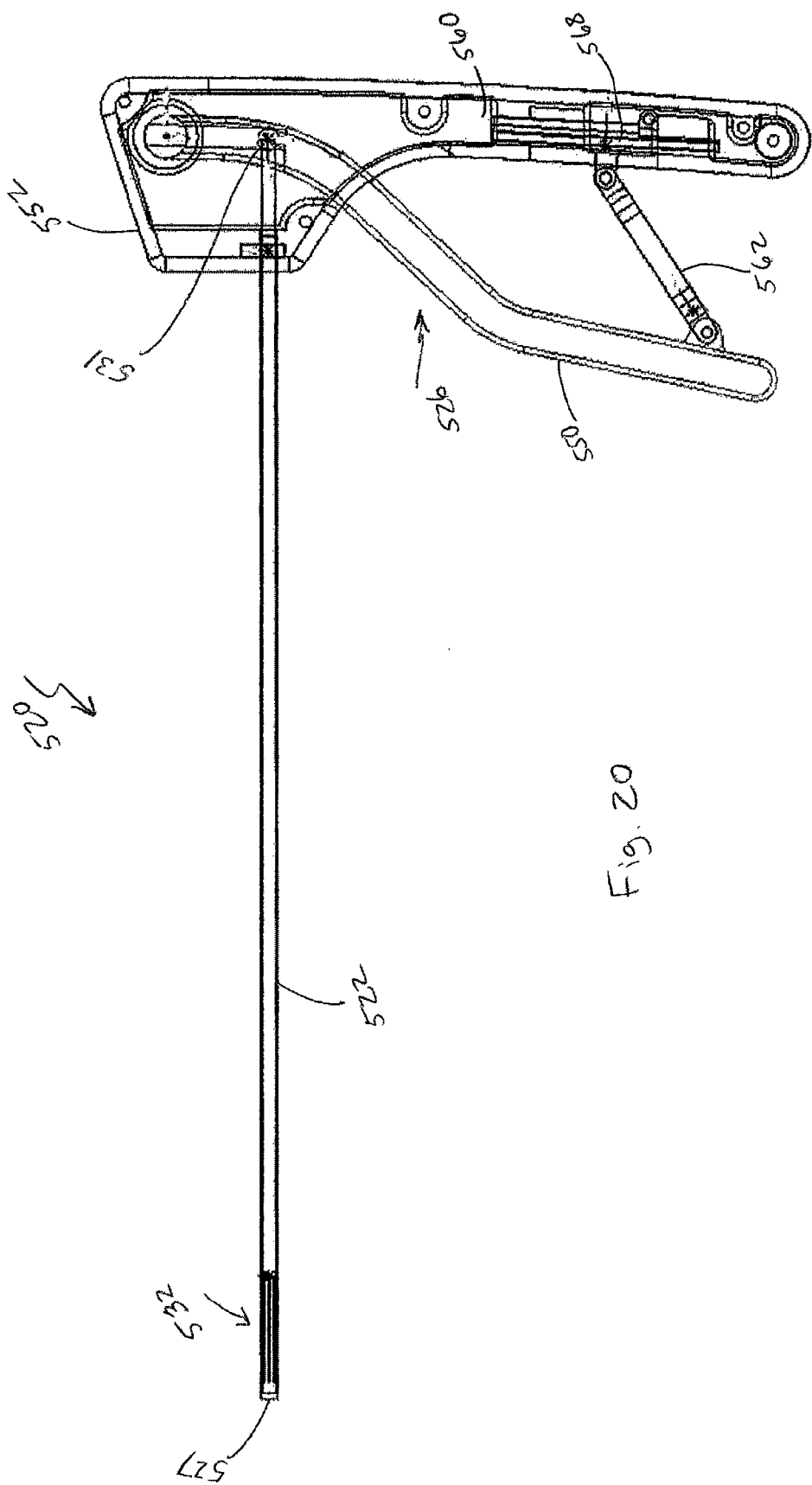
FIG. 20 is a side view of a medical device according to an embodiment of the invention shown in a collapsed configuration.
Figure 21:
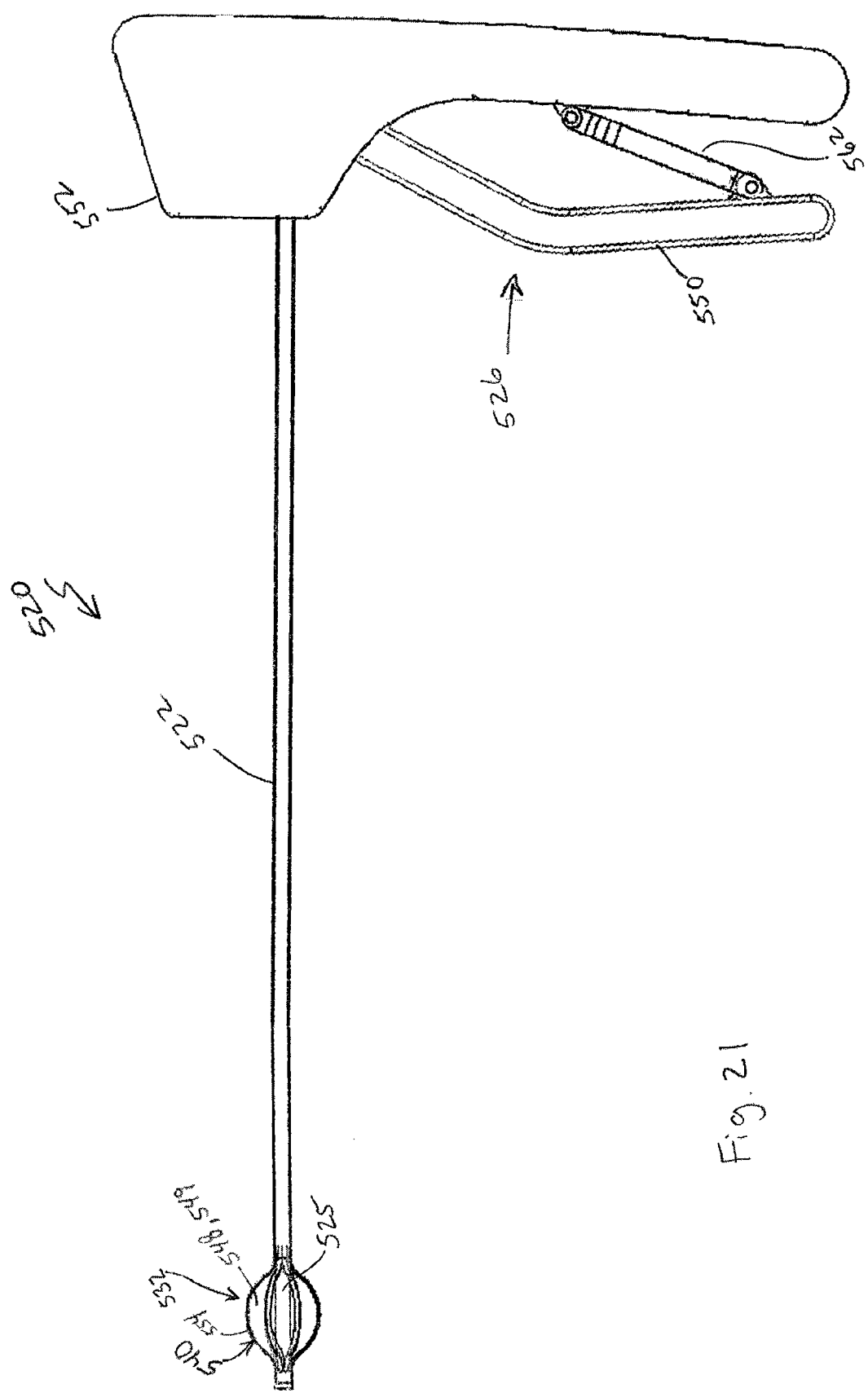
FIG. 21 is a side view of the medical device of FIG. 20 shown in an expanded configuration.

FIGS. 20 and 21 illustrate an embodiment of a medical device having a pull-rod that can be used to actuate the medical device between a collapsed configuration and an expanded configuration. In this embodiment, a handle of the medical device is gripped to move the medical device to an expanded configuration and released to move the medical device to a collapsed configuration. A medical device 520 includes an elongate body 522 movable between a collapsed configuration as shown in FIG. 20, and an expanded configuration as shown in FIG. 21. The elongate body 522 defines a lumen (not shown) and has a distal end portion 532 that includes multiple arms 540 that define openings 548 therebetween. An edge of the arms 540 define cutting portions 554. The medical device 520 also includes a rod 525 that is at least partially disposed within the lumen of the elongate body 522. A distal end (not shown) of the rod 525 is coupled to a distal end 527 of the elongate body 522 and a proximal end 531 of the rod 525 is coupled to an actuator 526.

As with the previous embodiment, the elongate body 522 can be foamed with a shape-memory material, such as Nitinol. In this embodiment, the elongate body 532 can be configured such that the distal end portion 532 of the elongate body 522 is biased into the collapsed configuration as shown in FIG. 20. The elongate body 522 can be formed in the same manner as described in the previous embodiment, for example, from a tubular member that has slits or windows cut in the distal end portion 532 to form the arms 540. When the elongate body 520 is in the expanded configuration, the arms 540 define an interior region or volume 549 that is larger than when the elongate body 522 is in the collapsed configuration.

The actuator 526 includes a handle 550 and a housing 552. FIG. 20 shows the medical device 520 with a portion of the housing 552 removed so that a portion of an interior of the medical device 520 can be viewed. In this embodiment, the handle 550 is operatively coupled to the rod 525, which is used to move the elongate body 522 between its expanded and collapsed configurations. The handle 550 is coupled to a slide member 568 via a pivot arm 562. The slide member 568 is also coupled to a spring (not shown), such as a compression spring, that is disposed within a compartment 560. The slide member 568 can move or translate back-and-forth as in the previous embodiment, as the spring moves between a biased position and a compressed position. The spring in its biased position, biases the handle 550 to an open position as shown in FIG. 20, and the rod 525 will be moved distally to a position as shown in FIG. 20. In this position, the elongate body 522 will be in its collapsed configuration.

To move the elongate body 522 from the collapsed configuration to the expanded configuration, the user grips the handle 550 such that the handle 550 is moved toward the housing 552, as shown in FIG. 21. This action will compress the spring, and move the rod 525 proximally, which in turn will cause the distal end portion 532 (e.g., arms 540) of the elongate body 522 to move to its expanded configuration.

As with the previous embodiments, when in the collapsed configuration, the medical device 520 can be inserted into a tissue of a patient, such as a vertebral body. For example, the medical device 520 can be inserted through an access cannula and to a desired location within a tissue. While disposed within the tissue, the user can grip the handle 550 to move the medical device 520 to the expanded configuration. In the expanded configuration, the medical device 520 can be rotated or otherwise moved within the tissue such that the cutting portions 554 of the arms 540 scrape, tear, or otherwise disrupt tissue, such as cancellous bone, within the tissue. In this embodiment, to move the medical device 520 back to the collapsed configuration, the user releases the handle 550.

Figure 22:
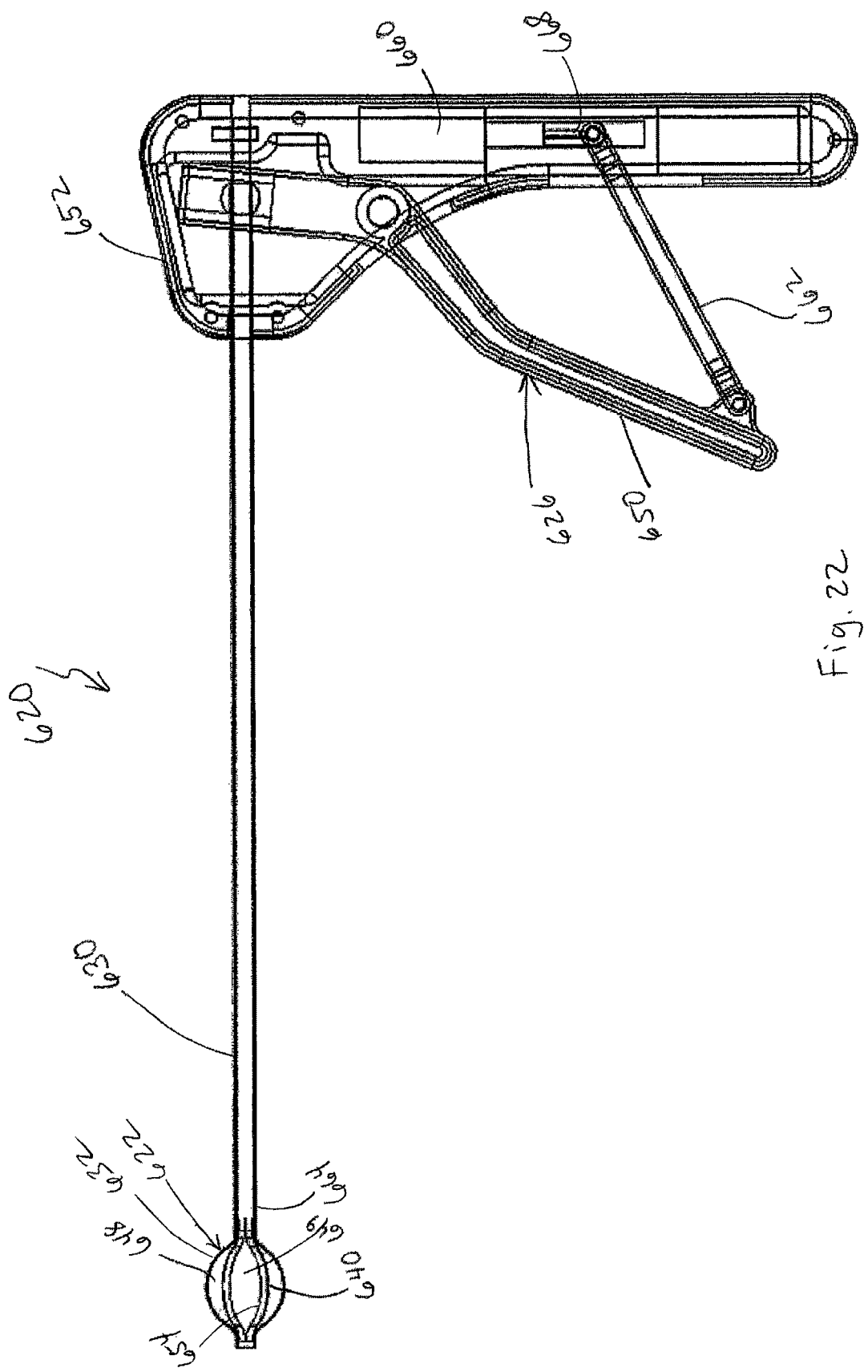
FIG. 22 is aside view of a medical device including a cut-away view of the handle according to an embodiment of the invention shown in an expanded configuration.

FIG. 22 illustrates an embodiment of a medical device similar to the medical device 220 (see FIGS. 14 and 15), except in this embodiment, the medical device includes only a single elongate body that is movable between a collapsed and expanded configuration by actuation of a sheath. A medical device 620 includes an elongate body 622 disposed within a lumen (not shown) of a sheath 630. The elongate body 622 is movable between a collapsed configuration (not shown) and an expanded configuration as shown in FIG. 22.

In this embodiment, the elongate body 622 has a distal end portion 632 that includes multiple arms 640 that define openings 648 therebetween. The arms 640 define cutting portions 654 disposed on an edge of the arms 640. As with the previous embodiments, the elongate body 622 defines an interior region or volume 649 that is larger when the elongate body 622 is in the expanded configuration than when it is in the collapsed configuration. The elongate body 622 can be formed in the same manner as described in the previous embodiment, for example, from a tubular member that has slits cut in the distal end portion 632 to form the arms 640. The elongate body 622 is also formed with a shape memory material, such as Nitinol, such that the distal end portion 632 can be biased to assume the expanded configuration.

The medical device 620 also includes an actuator 626 that includes a handle 650 that can be actuated by a user and a housing 652. In this embodiment, the handle 650 is operatively coupled to the sheath 630 and to a slide member 668 via the pivot arm 662. The slide member 668 is coupled to a spring (not shown), that biases the handle 650 to an open position as shown in FIG. 22. With the handle 650 is moved to its open position, the sheath 630 of the medical device 620 will be moved proximally such that a distal end 664 of the sheath 630 uncovers at least a portion of the distal end portion 632 to be moved to the expanded configuration.

To move the medical device 620 from the expanded configuration to the collapsed configuration, the user grips the handle 650 such that the handle 650 is moved toward the housing 652. This action will move the sheath 630 distally to a position (not shown) in which the distal end 664 of the sheath 630 is positioned substantially over the distal end portion 632 of the first elongate body 622. Thus, the distal end portion 632 of the elongate body 622 will be constrained in its collapsed configuration within the lumen of the sheath 630.

As with the previous embodiments, when in the collapsed configuration, the medical device 620 can be inserted (e.g., through an access cannula) and into a tissue of a patient. While disposed within the tissue, the user can release the handle 650 to move the medical device 620 to the expanded configuration. This action will move the distal end 664 of the sheath 630 proximally such that the distal end portion 632 of the elongate body 622 is disposed outside the lumen of the sheath 630, and automatically biased to its expanded configuration, as shown in FIG. 22. In the expanded configuration, the medical device 620 can be rotated or otherwise moved within the tissue such that the cutting portions 654 of the elongate body 622 scrape, tear, or otherwise disrupt tissue, such as cancellous bone, within the tissue. The medical device 620 can then be moved back to the collapsed configuration to remove the medical device 620 from the tissue.

Figure 23:
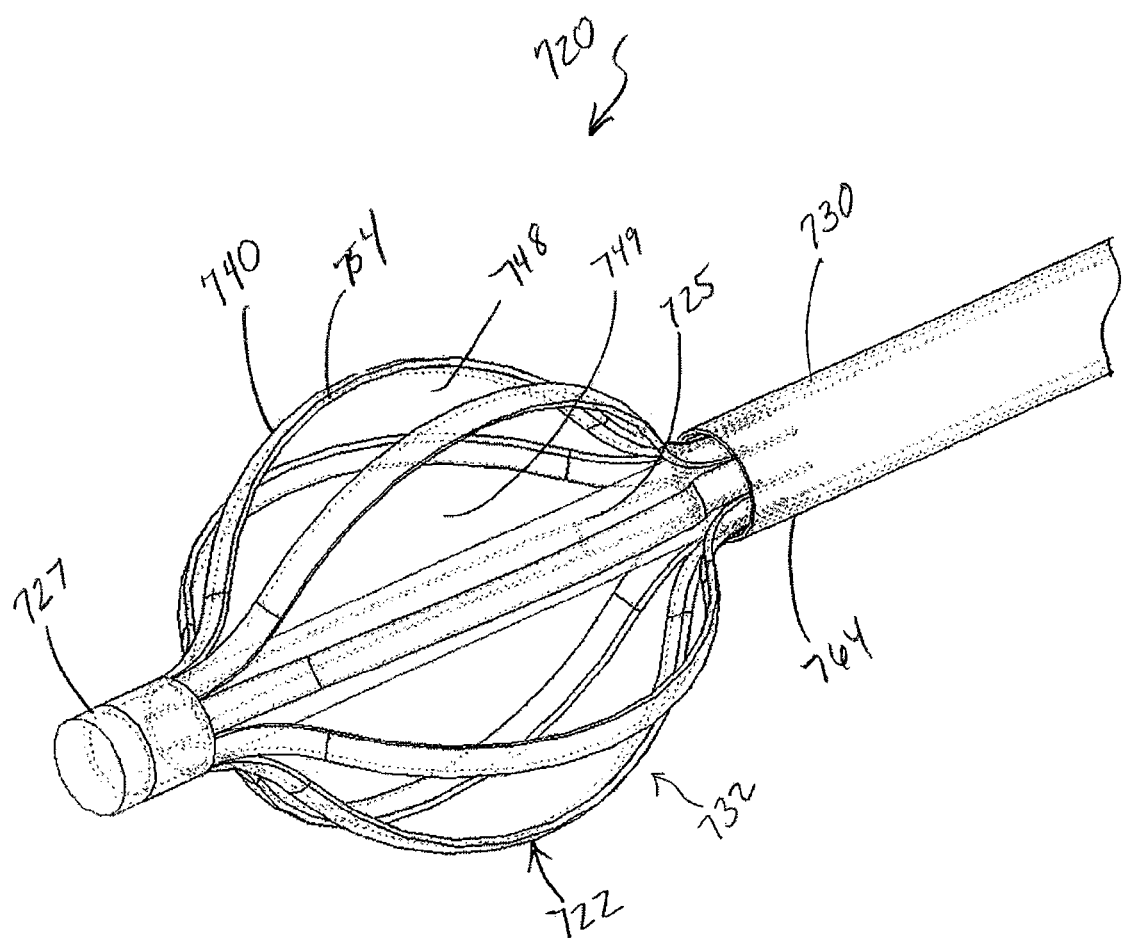
FIG. 23 is a side perspective view of a portion of a medical device according to another embodiment of the invention shown in an expanded configuration.
Figure 24:
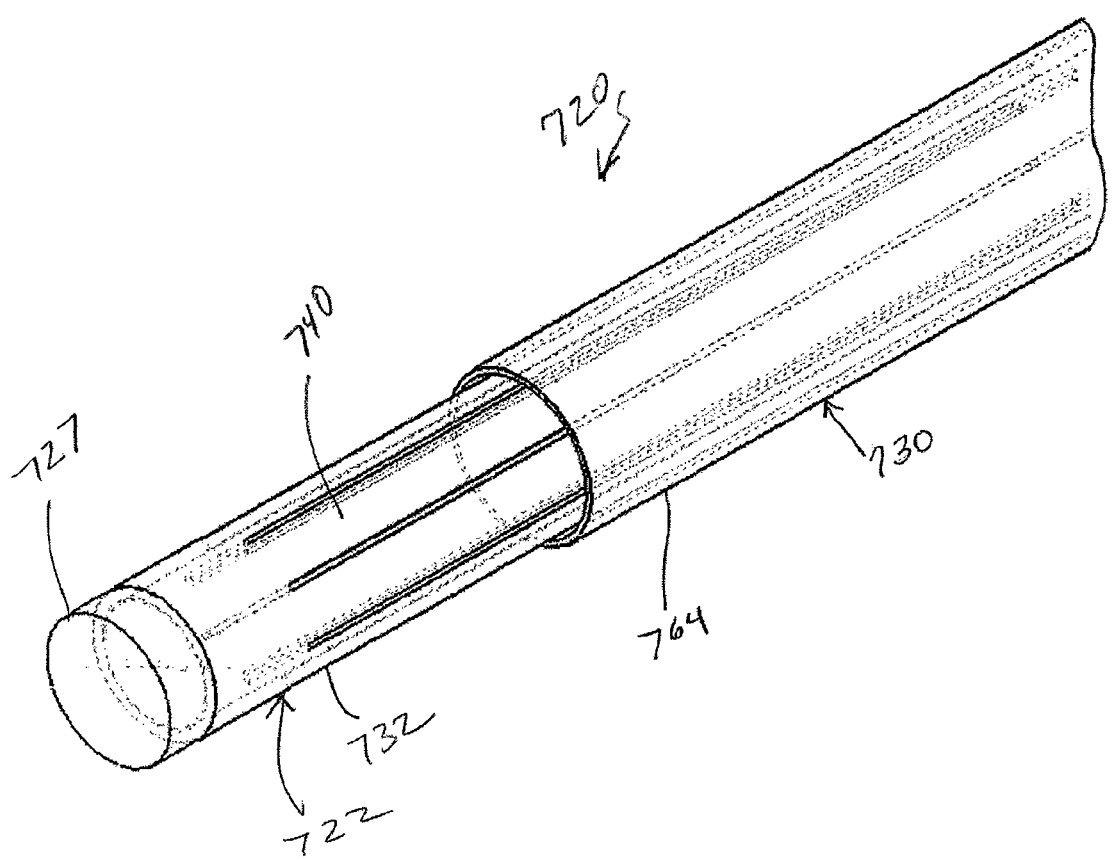
FIG. 24 is a side perspective view of the portion of the medical device of FIG. 23 shown in a collapsed configuration.

FIGS. 23 and 24 each illustrate a distal end portion of an embodiment of a medical device that can be used to disrupt tissue as described above, and can also be used to reduce a fracture of a vertebra. A medical device 720 includes both a pushrod and a sheath for actuation of the medical device 720 between a collapsed configuration and an expanded configuration. When deployed within a tissue in an expanded configuration, the medical device 720 is capable of applying force to surrounding tissue, including bone such that at least a portion of the tissue is distracted.

Specifically, as shown in FIG. 23, the medical device 720 includes an elongate body 722, a sheath 730 and a rod 725. As with the medical device 620, the elongate body 722 is movably disposed within a lumen (not shown) of the sheath 730. As with the medical devices 420 and 520, the rod 725 is disposed within a lumen (not shown ) of the elongate body 722.

The elongate body 722 can be formed with a shape memory material, such as Nitinol, in the same manner as described for previous embodiments. The elongate body 722 includes a distal end portion 732 that includes arms 740 that can be formed by cutting slots or windows into a wall of the elongate body 722. The arms 740 define openings 748 and an interior region 749. The arms 740 also include a cutting portion 754 disposed, for example, on an edge of the arms 740.

A distal end (not shown) of the rod 725 is coupled to a distal end 727 of the elongate body 722, and a proximal end (not shown) of the rod 725 is coupled to an actuator (not shown). The actuator can be for example, an actuator as described above for previous embodiments. The sheath 730 is also coupled at a proximal end (not shown) to the actuator. The actuator can be used to move both the rod 725 and the sheath 730 in the same manner as described for previous embodiments to move the medical device 720 between a collapsed configuration and an expanded configuration.

In this embodiment, the distal end portion 732 of the elongate body 722 is pre-set (or biased) into the expanded configuration. In use, to insert the medical device 720 into a tissue, a handle (not shown) of the actuator can be gripped such that the sheath 730 and the rod 725 are both moved or translated distally (e.g., substantially simultaneously). As shown in FIG. 24, a distal end 764 of the sheath 730 will move to a position covering at least a portion of the distal end portion 732 of the elongate body 722 causing the distal end portion 732 to at least partially collapse. Simultaneously, as the rod 725 is moved distally, the rod 725 will cause the distal end portion 732 of the elongate body 722 to straighten to the collapsed configuration. Once at the desired location at a tissue site, the handle of the actuator can be released, which will cause the rod 725 and sheath 730 to move proximally. The distal end portion 732 of the elongate body 722 will then be unconstrained by the sheath 730 and allowed to assume its biased expanded configuration, as shown in FIG. 23. At the same time, the rod 725 will force the distal end portion 732 of the elongate body 722 to the expanded configuration. Thus, the rod 725 will increase the rate at which, and the force with which the distal end portion 732 of the elongate body 722 will move to the expanded configuration.

The use of both the pushrod 725 and sheath 730 to actuate the movement of the elongate body 722 from the collapsed configuration to the expanded configuration, allows the medical device 720 to apply a greater force to the surrounding tissue during actuation. This can be beneficial, for example, when used in hard bone such as vertebral end plates.

Figure 25:
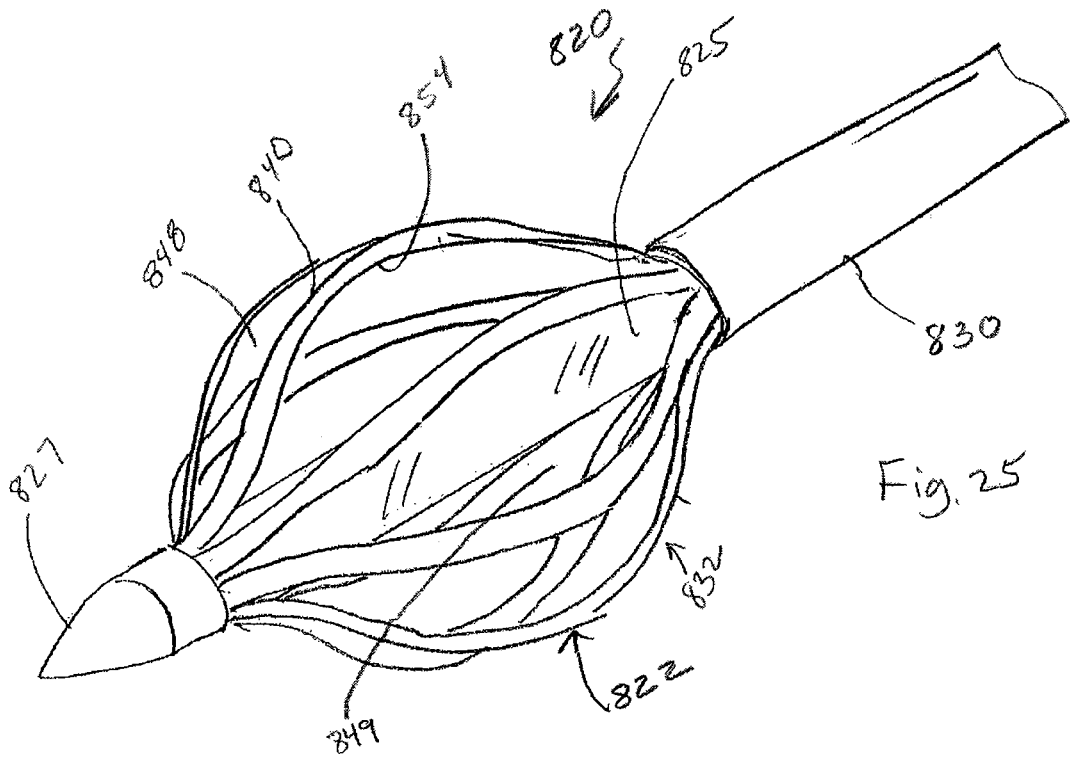
FIG. 25 is a side perspective view of a portion of a medical device according to another embodiment of the invention shown in an expanded configuration.
Figure 26:
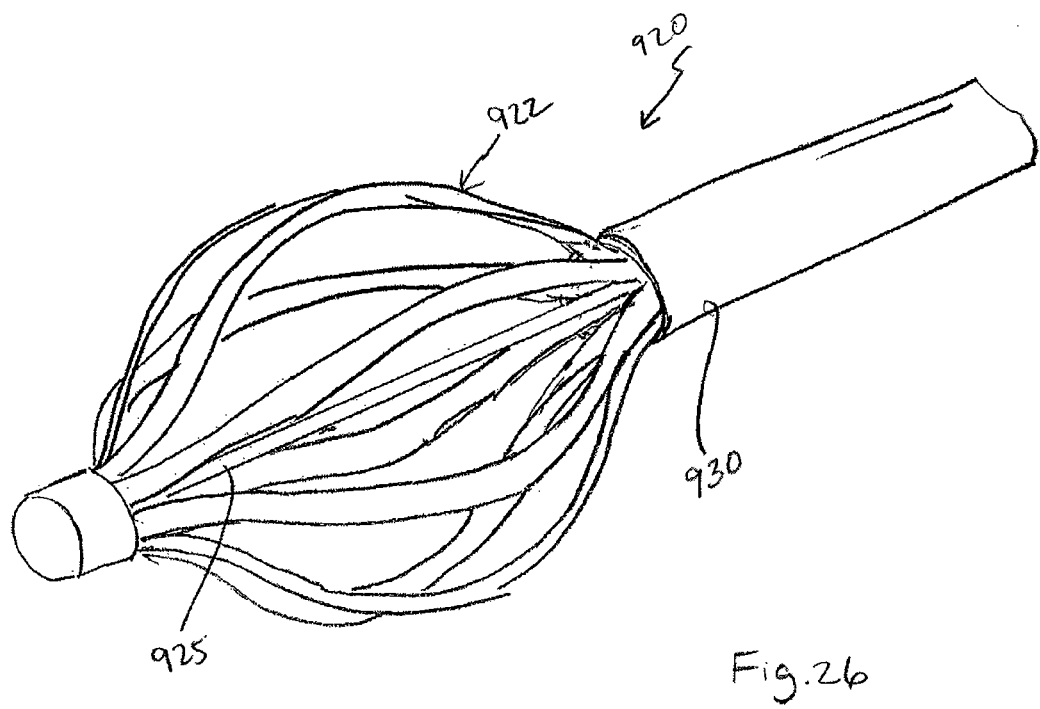
FIG. 26 is a side perspective view of a portion of a medical device according to another embodiment of the invention shown in an expanded configuration.
Figure 27:
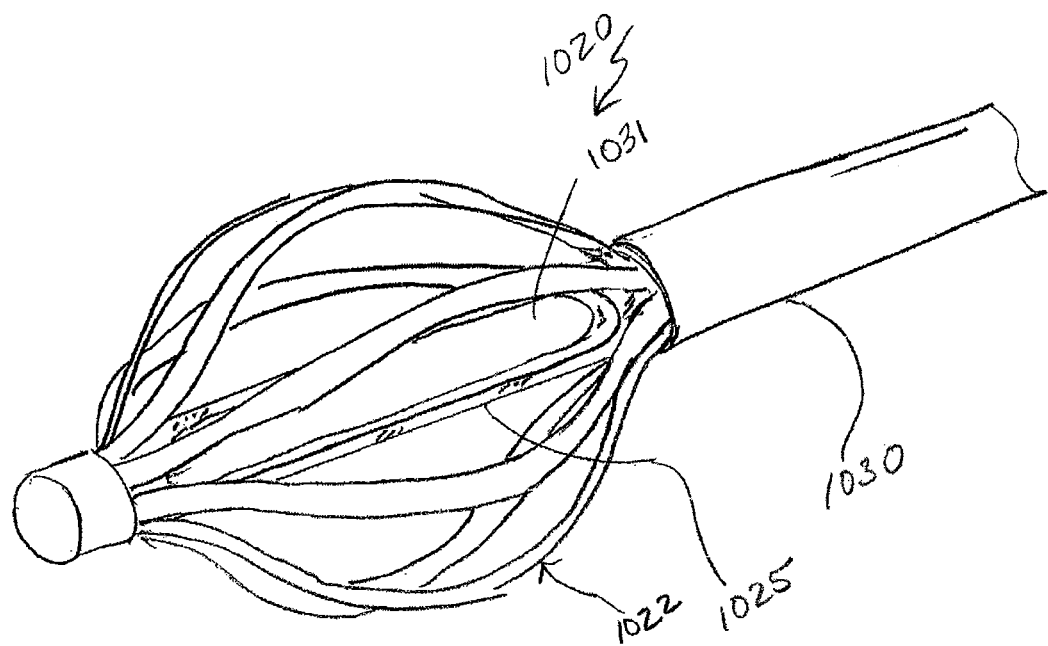
FIG. 27 is a side perspective view of a portion of a medical device according to another embodiment of the invention shown in an expanded configuration.

FIGS. 25-27 each illustrate a distal end portion of further embodiments of a medical device having both a rod and a sheath for actuation of the medical device between an expanded configuration and a collapsed configuration. Each of the medical devices described with reference to FIGS. 25-27 can include an actuator as described above to actuate both the rod and the sheath and to move the elongate body between an expanded configuration and a collapsed configuration. Each of the medical devices of FIGS. 25-27 can be used to disrupt tissue, and can also be used as a fracture reduction device as described above.

As shown in FIG. 25, a medical device 820 includes an elongate body 822, a sheath 830 and a rod 825. The elongate body 822 is disposed within a lumen (not shown) of the sheath 830. The rod 725 is disposed within a lumen (not shown) of the elongate body 822. The elongate body 822 can be formed with a shape memory material, such as Nitinol, in the same manner as described for previous embodiments, such that it is preset to assume an expanded configuration as shown in FIG. 25. The elongate body 822 includes a distal end portion 832 that includes arms 840 that can be formed by cutting slots or windows into a wall of the elongate body 822. The arms 840 define openings 848 and an interior region 849. The arms 840 also include a cutting portion 854 disposed, for example, on an edge of the arms 840.

A distal end (not shown) of the rod 825 is coupled to a distal end 827 of the elongate body 822, and a proximal end (not shown) of the rod 825 is coupled to an actuator (not shown). In this embodiment, the distal end 827 is tapered such that it can be used to penetrate tissue. In such an embodiment, a separate tool to penetrate tissue is unnecessary. The actuator can be for example, an actuator as described above for previous embodiments. The sheath 830 is also coupled at a proximal end (not shown) to the actuator. The actuator can be used to move both the rod 825 and the sheath 830 in the same manner as described for the previous embodiments, to move the medical device 820 between a collapsed configuration and an expanded configuration.

In an alternative embodiment, the rod can include an interior lumen with an opening in communication with the lumen at both a distal end and a proximal end of the rod. In such an embodiment, the distal end of the elongate body can define an opening in communication with the opening in the rod. Fluid can be introduced through the lumen of the rod and into a tissue via the distal openings of the rod and the elongate body. The lumen of the rod, and the distal openings in both the rod and the elongate body can also be used for suction of material out of the tissue. In some embodiments, the distal end of the elongate body can have multiple openings. For example, a syringe can be coupled to a proximal end of the rod and can be used to introduce a saline solution and/or to provide suction to remove, for example, tissue fragments from within the interior region of the distal end portion (e.g., expanded portion) of the elongate body.

FIG. 26 illustrates a medical device 920 that includes a sheath 930, an elongate body 922 and a rod 925. The medical device 920 is constructed in the same manner as described above for the previous embodiment except in this embodiment, the rod 925 has a smaller diameter than the embodiments of a rod (e.g., 825, 725) described above. The smaller diameter of rod 925, for example, provides additional space within a lumen of the elongate body 922 for the insertion of other devices, or for the addition of functions to the medical device 920. For example, a suction device and/or an irrigation device can be coupled to a proximal end of the elongate body 922 and provide for the introduction of fluid through the lumen of the elongate body and into a tissue, and/or removal of tissue (e.g., bone fragments, nucleus material), and/or fluid (e.g., irrigation fluid) out of the tissue. In some embodiments, a separate device that provides suction and/or irrigation can be inserted through the lumen of the elongate body 922.

FIG. 27 illustrates a medical device 1020 that includes a sheath 1030, an elongate body 1022 and a rod 1025. The medical device 1020 is constructed in the same manner as described above for the previous embodiments except in this embodiment, the rod 1025 defines a lumen (not shown) and at least one window 1031 in communication with the lumen. The lumen of the rod 1025 can provide for the insertion of other devices, or for the addition of functions to the medical device 1020. For example, an irrigation device can be coupled to a proximal end of the rod 1025 and provide for the introduction of fluid through the lumen of the elongate body and into a tissue.

In some embodiments, a suction device can be coupled to a proximal end of the rod and provide suction force to removal tissue (e.g., bone fragments, nucleus material), and/or fluid (e.g., irrigation fluid) out of the tissue. For example, as the medical device 1020 is used to cut or disrupt tissue, the cut or disrupted portions of tissue can be drawn through the window(s) 1031 and into the lumen of the rod 1025. In some embodiments, other tools, such as a rod with threaded distal portion can be introduced through the lumen of the rod 1025 and used to remove trapped tissue fragments (e.g., bone fragments). For example, the rod can be rotated such that tissue fragments are captured by the threaded portion of the rod through the window(s) 1031.

FIGS. 28-33 illustrate two embodiments of a medical device having an elongate member that can be used to clear bone or other tissue out from within an interior region of the expandable portion of the medical device. As shown in FIGS. 28-33, a medical device 1120 includes a sheath 1130 coupled to an actuator 1126, and an elongate body 1122. As with previous embodiments, the elongate body 1122 is at least partially disposed within a lumen (not shown) of the sheath 1130. The elongate body 1122 includes a distal end portion 1132 having multiple arms 1140 that define openings 1148 and an interior region 1149. The arms 1140 can be formed in the same manner as described for previous embodiments. The interior region 1149 is in communication with a lumen (not shown) defined by the elongate body 1122 that extends to a proximal end of the elongate body 1122.

As with previous embodiments, the actuator 1126 includes a housing 1152, a handle 1150 and a pivot arm 1162. The actuator 1126 can be used in the same manner as described previously to actuate or translate the sheath 1130 proximally and distally, which in turn moves the distal end portion 1132 of the elongate body 1122 between a collapsed configuration and an expanded configuration.

In this embodiment, the medical device 1120 also includes an elongate member 1174, as best shown in FIG. 29. The elongate member 1174 is movably disposable within the lumen of the elongate body 1122 as shown in FIGS. 28 and 30. As shown in FIG. 28, the elongate member 1174 can be inserted through an opening 1176 in the housing 1152, and extend through the lumen of the elongate body 1122. A distal end portion 1178 of the elongate member 1174 can exit the lumen of the elongate body at a location within the interior region 1149. The elongate member 1174 can be used to push or move tissue fragments from within the interior region 1149 and out through the openings 1148 defined by the arms 1140. For example, when the medical device 1120 is used to scrape or disrupt tissue as described above for previous embodiments, tissue fragments can possibly become disposed within the interior region 1149. The elongate member 1174 can be moved distally to move at least a portion of the tissue fragments out of the interior region 1149 in some instances. The elongate member 1174 can be moved proximally and distally or removed and inserted repeatedly, as desired, to tamp out tissue fragments inside the interior region 1149. In some embodiments, the elongate member 1174 can be actuated by an actuator such that it oscillates back and forth. In some embodiments, the elongate member 1174 can be actuated such that it is moved distally as the distal end portion 1132 of the elongate body 1122 is moved from the expanded configuration to the collapsed configuration.

The elongate member 1174 can include a handle 1173 that can be grasped by a user to assist in moving the elongate member 1174 proximally and/or distally within the lumen of the elongate body 1122. The elongate member 1174 can have a length such that a distal end 1171 of the elongate member 1174 can extend to a distal end of the elongate body 1122, while the handle 1173 is disposed proximally of the housing 1152. Although the distal end 1171 of the elongate member 1174 is shown substantially flat or planar, in alternative embodiments, the distal end 1171 can be rounded or curved. The distal end 1171 can also include a trocar, bevel, of other sharp tip to cut though tissue, such as bone, as it pushes fragments out of the interior region 1149.

In alternative embodiments, an elongate member can have a collapsed configuration and an expanded configuration. For example, a distal end portion of the elongate member can have expandable arms similar to the distal end portion (e.g., 1132) of an elongate body (e.g., 1122). In such an embodiment, the elongate member can be moved from its collapsed configuration to its expanded configuration when the distal end portion of the elongate member is disposed within the interior region of the elongate body, and the expanded distal end portion of the elongate member can displace tissue fragments out of the interior region of the elongate body. In such an embodiment, the elongate member can be moved between its collapsed and configurations with, for example, an actuator. The actuator can include a trigger to manually actuate the elongate member. Alternatively, the actuator can be motorized such that it can be actuated automatically.

FIGS. 31-33 illustrate a medical device 1220 that is similar to the medical device 1120. The medical device 1220 includes a sheath 1230 coupled to an actuator 1226, and an elongate body 1222. As with previous embodiments, the elongate body 1222 is at least partially disposed within a lumen (not shown) of the sheath 1230, and includes a distal end portion 1232 having multiple arms 1240. The arms 1240 define openings 1248 and an interior region 1249. The arms 1240 can be formed in the same manner as described for previous embodiments. The interior region 1249 is in communication with a lumen (not shown) defined by the elongate body 1222, and that extends to a proximal end of the elongate body 1222.

The actuator 1226 includes a housing 1252, a handle 1250 and a pivot arm 1262. The actuator 1226 can be used in the same manner as described previously to actuate or translate the sheath 1230 proximally and distally, which in turn moves the distal end portion 1232 of the elongate body 1222 between a collapsed configuration and an expanded configuration.

The medical device 1220 also includes an elongate member 1274, as best shown in FIG. 32. The elongate member 1274 is movably disposable within the lumen of the elongate body 1222. The elongate member 1274 is inserted through an opening (not shown) in the housing 1252, and extends through the lumen of the elongate body 1222. In this embodiment, the elongate member 1274 defines an interior lumen (not shown) and multiple openings 1275 at a distal end portion 1278. The distal end portion 1278 of the elongate member 1274 can exit the lumen of the elongate body 1222 within the interior region 1249 as shown in FIG. 33. The elongate member 1274 can be used in the same manner as described above for elongate member 1174 to push, displace, dislodge, or move tissue fragments from within the interior region 1249 and out through the openings 1248 defined by the arms 1240. In addition, a fluid, such as a saline solution, can be introduced into the lumen of the elongate member 1274, through the openings 1275 and into the interior region 1249.

A proximal end 1277 of the elongate member 1274 includes a handle 1273 that includes a fitting 1269. The fitting 1269 can be, for example, a luer fitting molded into the handle 1273. The fitting 1269 can be used to couple a syringe to the elongate member 1274 that can be used to introduce fluid (e.g., saline) to the elongate member 1274. In use, after the medical device 1220 is used to scrape or disrupt tissue, the elongate member 1274 can be used as described above to clear tissue fragments from the interior region 1249. Fluid can also be injected through the elongate member 1274 and used to assist in clearing tissue fragments from within the interior region 1249 and out through the openings 1248. A device configured to provide suction can also optionally be coupled to the fitting 1269 and used to suction tissue fragments out of the interior region 1249. In such an embodiment, depending on the type of tissue being disrupted, it may be desirable for the openings 1275 to be larger in size than shown in FIGS. 31 and 32 to allow the tissue fragments to pass through.

FIGS. 34 and 35 illustrate an embodiment of a medical device having a different type of actuator than previously described. A medical device 1320 includes an elongate body 1322, a sheath 1330 and an actuator 1326. As shown in FIG. 35, the elongate body 1322 includes a distal end portion 1332 that has multiple arms 1340 that can move between a collapsed configuration and an expanded configuration. The arms 1340 define openings 1348 and an interior region 1449. The sheath 1330 defines a lumen (not shown), through which the elongate body 1322 is disposed.

The actuator 1326 includes a first member 1365 operatively coupled to a second member 1367 via a pair of biasing mechanisms 1363. The biasing mechanisms 1363 can include, for example a spring (not shown) configured to bias the actuator 1326 into a first configuration. In the first configuration, the first member 1365 and the second member 1367 are biased into a first position relative to each other, as shown in FIG. 34. The sheath 1330 is coupled to the first member 1365 and/or the second member 1367, such that when the actuator 1326 is biased into the first configuration, the sheath 1330 is moved distally, and a distal end portion 1364 of the sheath 1364 is disposed over at least a portion of the distal end portion 1332 of the elongate body 1322. This action causes the arms 1340 of the distal end portion 1332 to collapse sufficiently to insert the medical device through, for example, an access cannula.

In use, the user can insert the medical device 1320 into a tissue site with the actuator 1326 in the first configuration, as shown in FIG. 34. The user can then squeeze the first member 1365 and the second member 1367 together, which will move the actuator to a second configuration, as shown in FIG. 35. This action will draw the sheath 1330 proximally, such that the distal end portion 1332 of the elongate body 1322 is no longer constrained within the sheath 1330 and can assume its expanded configuration. With the distal end portion 1332 of the elongate body 1322 in the expanded configuration, the medical device 1320 can be used to disrupt or scrape tissue as previously described. To remove the medical device 1320 from the tissue, the user discontinues squeezing the first member 1365 and the second member 1367 together, which will move the actuator 1326 to the first position as shown in FIG. 34.

In an alternative embodiment, the elongate body can be movably coupled to the actuator, instead of the sheath. In such an embodiment, when the actuator is in the first configuration (e.g., FIG. 34), the elongate body will be moved proximally such that a distal end portion of the elongate body is at least partially collapsed within a lumen of the sheath. When the actuator is moved to the second configuration (e.g., FIG. 35), the elongate body will be moved distally, such that the distal end portion is disposed outside of the lumen of the sheath. Although not shown, this embodiment of a medical device can also include an elongate member, such as elongate member 1174 or 1274 discussed above.

Figure 36:
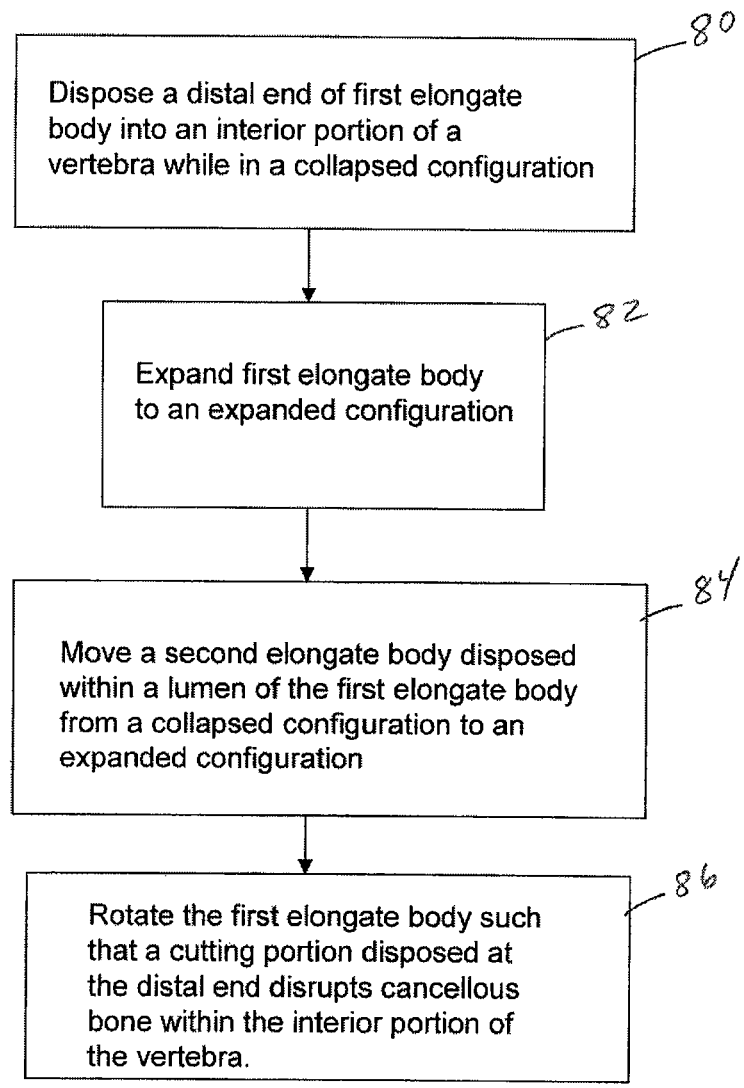
FIGS. 36-38 are each a flowchart illustrating a method according to different embodiments of the invention

FIG. 36 is a flowchart illustrating a method according to an embodiment of the invention. In one example, a method includes at 80, disposing a distal end portion of a first elongate body while in a collapsed configuration at least partially into an interior of a vertebra. The first elongate body has a cutting portion disposed on a distal end portion. The first elongate body is expanded to an expanded configuration at 82. Simultaneously with expanding the first elongate body, a second elongate body that is disposed within a lumen of the first elongate body is moved from a collapsed configuration to an expanded configuration at 84. At 86, the first elongate body is rotated while in the expanded configuration such that the cutting portion disrupts cancellous bone within the interior portion of the vertebra. The second elongate body is configured to prevent at least a portion of disrupted cancellous bone from being disposed within the first elongate body during the rotating of the first elongate body. In some embodiments, the expanding includes moving a volume of fluid from a reservoir to an interior portion of the second elongate body. In some embodiments, the first elongate body includes a plurality of arm members, and the second elongate body is configured to prevent at least a portion of disrupted cancellous bone from entering into an interior portion defined by the plurality of arm members during the rotating.

Figure 37:
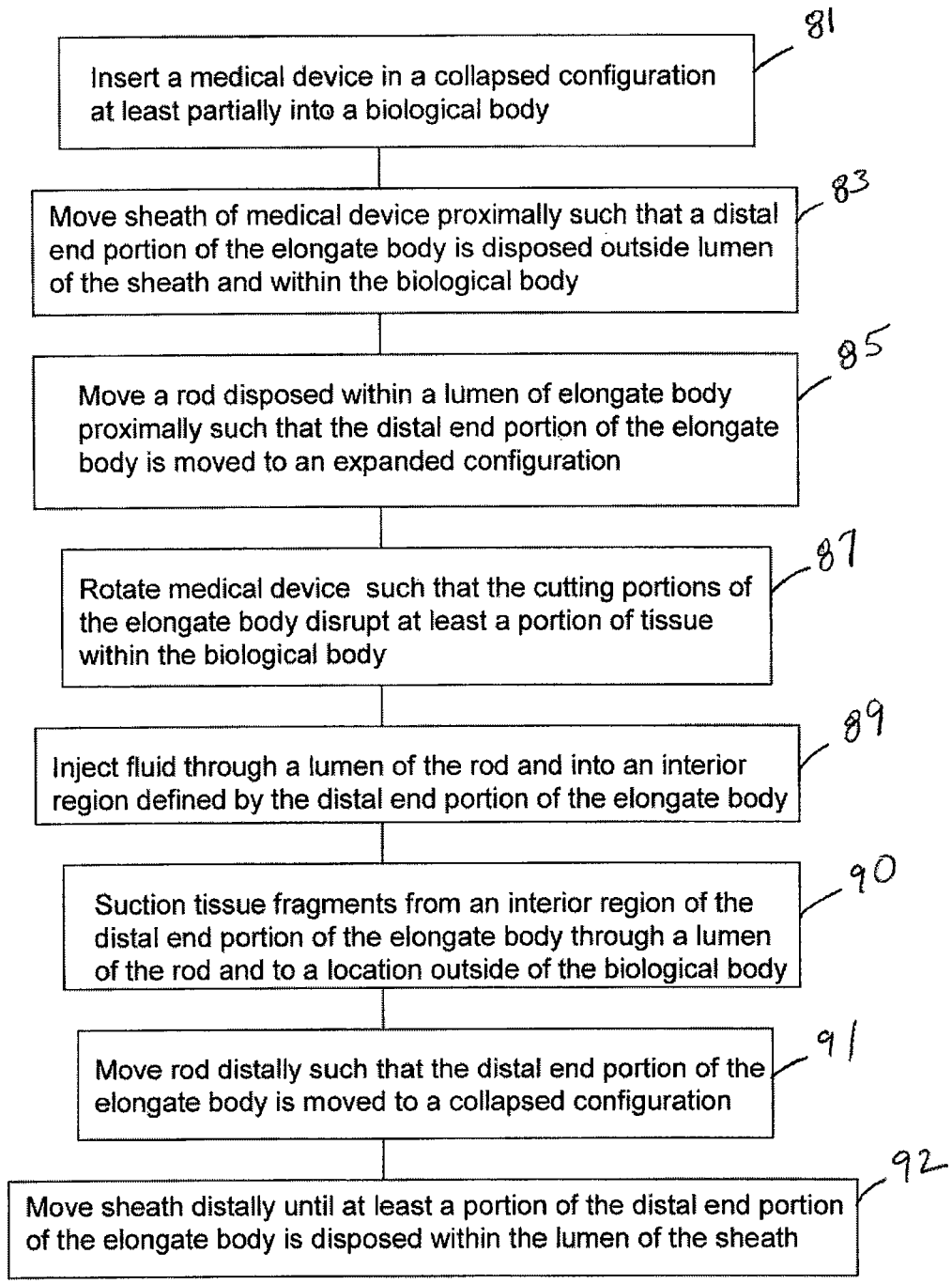

FIG. 37 is a flowchart illustrating a method according to another embodiment of the invention. In this example, a method includes at 81, inserting a medical device in a collapsed configuration at least partially into a biological body. The biological body can be, for example, a vertebra or an intervertebral disc. In some embodiments, during the inserting, at least a portion of tissue within the biological body can be penetrated with a distal end of the elongate body. The medical device can have a sheath and an elongate body at least partially disposed within a lumen of the sheath. The distal end of the elongate body can include a plurality of cutting portions. At 83 the sheath is moved proximally such that a distal end portion of the elongate body is disposed outside of the lumen of the sheath and within the biological body. Once outside of the lumen of the sheath, the distal end portion of the elongate body can assume a biased expanded configuration. At 85, in some embodiments, a rod that can optionally be disposed within a lumen of the elongate body can be moved proximally such that the distal end portion of the elongate body is moved to an expanded configuration. In such an embodiment, the rod can be moved simultaneously or sequentially with the moving of the sheath at 83.

At 87, with the distal end portion of the elongate body in the expanded configuration, the medical device can be rotated such that the cutting portions of the distal end portion of the elongate body disrupt at least a portion of tissue within the biological body. In some embodiments, the distal end portion of the elongate body in the expanded configuration can be used to distract at least a portion of tissue within the biological body.

In some embodiments, at 89, after rotating the medical device, a fluid can optionally be injected through a lumen of the rod and into an interior region defined by the distal end portion of the elongate body. In some embodiments, after the rotating the medical device, at 90 tissue fragments can optionally be suctioned from an interior region defined by the distal end portion of the elongate body through a lumen of the rod and to a location outside of the biological body. At 91, in an embodiment having an optional rod, after rotating the medical device, the rod can be moved distally such that the distal end portion of the elongate body is moved to a collapsed configuration. At 92, the sheath can be moved distally until at least a portion of the distal end portion of the elongate body is disposed within the lumen of the sheath.

Figure 38:
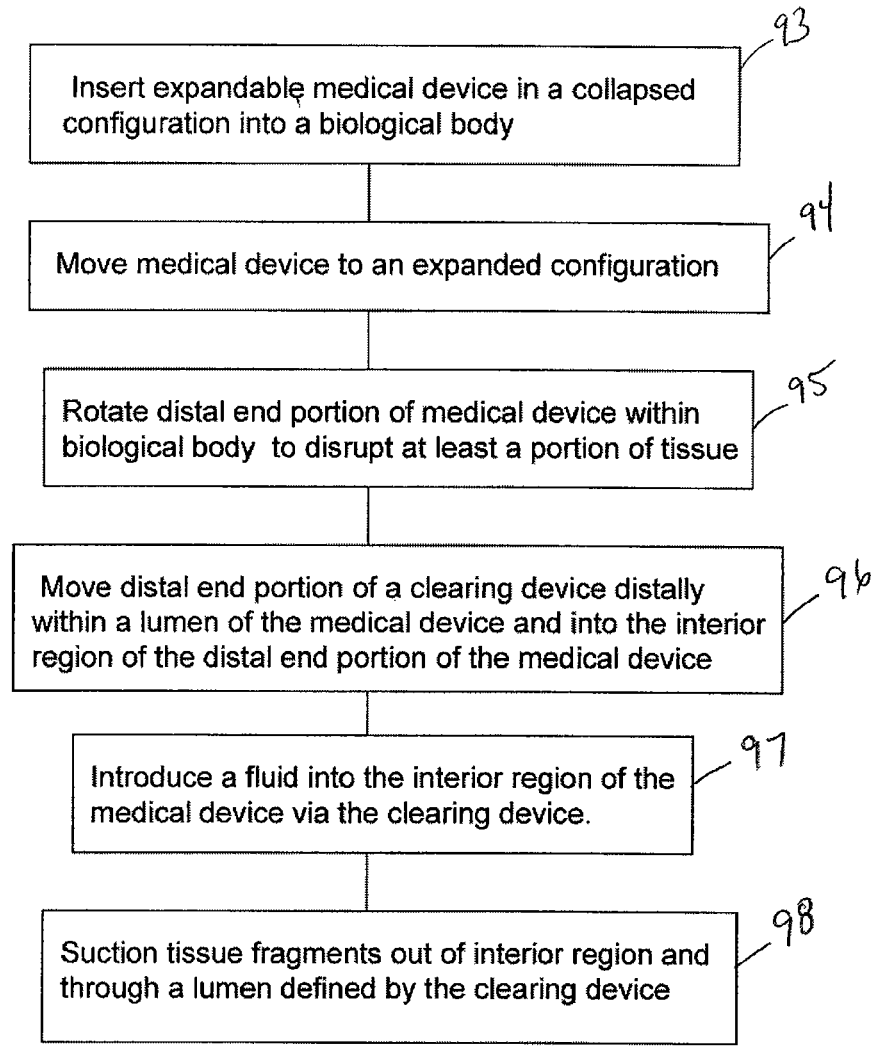

FIG. 38 illustrates a method according to yet another embodiment of the invention. In this example, a method includes at 93, inserting an expandable medical device in a collapsed configuration into a biological body, such as a vertebra or an intervertebral disc. The medical device can include, for example, an actuator that biases the medical device into an expanded configuration and that moves the medical device to the collapsed configuration when actuated. A distal end portion of the medical device defines a plurality of openings in communication with an interior region defined by the distal end portion of the medical device. In some embodiments, the medical device can include a tapered distal end that can penetrate tissue while inserting the medical device into the biological body. At 94, the medical device is moved to an expanded configuration. For example, an actuator can be released to allow the medical device to assume a biased or pre-set expanded configuration.

At 95, the distal end portion of the medical device is rotated within the biological body such that at least a portion of tissue within the biological body is disrupted. For example, the distal end portion of the medical device can include multiple arms configured to disrupt tissue when rotated. At 96, after rotating the medical device, a distal end portion of an elongate member can be moved distally within a lumen of the medical device and into the interior region of the distal end portion of the medical device. The elongate member can displace tissue fragments from the interior region. For example, the medical device can include multiple arms that define the interior region when the medical device is in the expanded configuration, and tissue fragments can be displaced through openings defined by the multiple arms of the distal end portion of the medical device. In some embodiments, at 97 a fluid can optionally be introduced into the interior region of the medical device via the elongate member. For example, the elongate member can define a lumen through which fluid can be introduced. In some embodiments, at 98 tissue fragments can optionally be suctioned out of the interior region and through a lumen defined by the elongate member.

The medical device for any of the embodiments may be constructed with any suitable material used for such a medical device. The elongate bodies for any embodiments can be formed with Nitinol, superelastic Nitinol, or other shape-memory material. The elongate bodies, the rods, the elongate members and the sheaths can each be formed with various biocompatible metal materials, such as stainless steel, titanium, titanium alloy, surgical steel, metal alloys, or suitable biocompatible plastic materials, such as various polymers, polyetheretherketone (PEEK), carbon fiber, ultra-high molecular weight (UHMW) polyethylene, etc., or various elastic materials, flexible materials, various rubber materials, or combinations of various materials thereof. The cutting member can likewise be constructed with suitable biocompatible metals or plastics. The flexible expandable member can be formed with various flexible or expandable materials such as plastics (e.g., various polymers) and/or rubber materials having flexible or expandable characteristics.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combinations of components, other embodiments are possible having a combination or sub-combination of any features and/or components from any of embodiments as discussed above. For example, the first elongate body and the second elongate body can each be moved between their collapsed and expanded configurations by means other than those described herein. For example, a medical device according to an embodiment described herein can be actuated with a separate actuator or device.

In addition, any of the embodiments of a medical device can include a ratchet mechanism operatively coupled to the actuator. This would allow the medical device to be actuated or expanded/collapsed at different increments and/or sizes. A medical device according to the invention can use more than one type of actuator. For example, a medical device can include a pushrod or a pullrod and a movable sheath in combination. Various types of different handles can also be used.

Further, the various components of a medical device as described herein can have a variety of different shapes and or size not specifically illustrated. For example, the distal end portions of the first elongate body and the second elongate body can have a variety of different shapes and sizes. A distal end portion of an elongate body that has a flexible membrane configuration (e.g., a balloon) can be, for example, circular, oval, square, rectangular, triangular, oblong, peanut shaped, etc. In another example, a distal end portion of an elongate body having a whisk-type configuration can be, for example, square, rectangular, oval, circular, triangular, etc. A medical device according to the invention can include one or more elongate bodies, one or more expandable portions, and/or one or more actuators.

Although the use of a medical device was described with a specific example of use within a vertebra, it should be understood that the medical device and methods described herein can be used in other areas of a patient, such as for example, within an intervertebral disc. For example, the medical device can be used in other areas within a spine, as well as other bone or soft tissue areas within a patient's body.

What is claimed is:

1. An apparatus, comprising:
a first expandable member including an elongate portion and an expandable portion defining a hollow interior region, the expandable portion being fixedly disposed at a distal end portion of the elongate portion, the distal end portion including an end cap comprising a closed distal end, the first expandable member configured to disrupt a body when in an expanded configuration and moved relative to the body; and
a second expandable member disposed within the interior region of the first expandable member and configured to block at least a portion of disrupted portions of the body from being disposed within the first expandable member when the second expandable member is expanded,
an actuator coupled to the first and second expandable members in a manner permitting the first expandable member to be expanded independently of the second expandable member upon actuation of the actuator.

2. The apparatus of claim 1, wherein the expandable portion of the first expandable member includes a plurality of arm members extending from the end cap, the plurality of arm members collectively defining an interior volume of the interior region and defining a plurality of openings in communication with the interior volume while the first expandable member is in the expanded configuration.

3. The apparatus of claim 1, wherein the expandable portion of the first expandable member includes a cutting portion, the cutting portion configured to disrupt the body when the first expandable member is moved relative to the body.

4. The apparatus of claim 1, wherein the second expandable member includes a cutting portion configured to disrupt the body when the second expandable member is moved relative to the body.

5. The apparatus of claim 1, wherein the expandable portion of the first expandable member includes a plurality of arm members extending from the end cap, the plurality of arm members collectively defining an interior volume of the interior region while the first expandable member is in the expanded configuration, the second expandable member is configured to block at least a portion of disrupted portions of the body from being disposed within the interior volume defined by the plurality of arm members.

6. The apparatus of claim 1, wherein the expandable portion of the first expandable member includes a plurality of arm members extending from the end cap, the plurality of arm members defining a plurality of openings, the second expandable member includes a plurality of ribs, the plurality of ribs configured to be positioned in an offset relationship with respect to the plurality of arm members when the first expandable member is in its expanded configuration and the second expandable member is in its expanded configuration such that the plurality of openings defined by the plurality of arm members are substantially closed by the plurality of ribs.

7. The apparatus of claim 1, wherein the second expandable member includes a flexible membrane, when the second expandable member is in its expanded configuration the flexible membrane is configured to block at least a portion of disrupted portions of the body from being disposed within the first expandable member.

8. The apparatus of claim 1, wherein the second expandable member includes a flexible member, the apparatus further comprising:
a reservoir in fluid communication with the flexible member, the flexible member and the reservoir forming a closed fluid system.

9. The apparatus of claim 1, wherein the second expandable member includes a flexible member, the apparatus further comprising:
a reservoir in fluid communication with the flexible member, the flexible member and the reservoir forming a closed fluid system; and
a volume of fluid disposed within the closed fluid system, the second expandable member being in its expanded configuration when a portion of the volume of fluid disposed within the flexible member is greater than a portion of the volume of fluid disposed within the flexible member when the second expandable member is in its collapsed configuration.

10. The apparatus of claim 1, further comprising:
a sheath coupled to the first expandable member, the first expandable member configured to be inserted at least partially into an interior portion of the body while the first expandable member is disposed within a lumen of the sheath, the sheath configured to be moved proximally while at least partially inserted into the interior portion of the body such that the first expandable member is moved from a collapsed configuration to its expanded configuration.

11. The apparatus of claim 1, wherein the body is a vertebra.

12. The apparatus of claim 1, wherein the expandable portion of the first expandable member is fixedly coupled to the elongate portion of the first expandable member.

13. The apparatus of claim 1, wherein the expandable portion of the first expandable member is formed monolithically with the elongate portion of the first expandable member.

14. The apparatus of claim 1, wherein the first expandable member is movable between a collapsed configuration and the expanded configuration, the first expandable member having a cylindrical cross section with a uniform width when in the collapsed configuration.

15. The apparatus of claim 1, wherein the second expandable member comprises a balloon that is movable between a collapsed orientation and an expanded orientation, wherein proximal and distal ends of the balloon have a maximum width that is greater than that of an intermediate portion of the balloon positioned between the proximal and distal ends of the balloon when the balloon is in the collapsed orientation.

16. The apparatus of claim 1, wherein the first expandable member comprises a shape memory material.

17. The apparatus of claim 1, wherein the second expandable member comprises a balloon disposed in the interior region and an elongate section disposed within the elongate portion, the balloon comprising a flexible material and the elongate section comprising a non-flexible material.

18. The apparatus of claim 1, wherein the second expandable member comprises a balloon disposed in the interior region and an elongate section disposed within the elongate portion, the balloon and the elongate section comprising a flexible material.

19. An apparatus, comprising:
an elongate body including a distal end portion defining a hollow interior region, the distal end portion having an expanded configuration and a collapsed configuration, the distal end portion including an end cap comprising a closed distal end, a plurality of arms extend between the end cap and the elongate body, each arm from the plurality of arms having a cutting portion, the cutting portion configured to disrupt tissue within a vertebra;

a flexible member having an expanded configuration and a collapsed configuration, at least a portion of the flexible member being disposed within the interior region of the elongate body;

a reservoir in fluid communication with the flexible member; and an actuator coupled to the reservoir and the elongate body, the actuator configured to actuate the elongate body between its collapsed configuration and its expanded configuration while simultaneously actuating movement of fluid contained within the reservoir and the flexible member to actuate the flexible member between its collapsed configuration and its expanded configuration, the actuator operable to independently control expansion of the distal end portion and the flexible member such that the distal end portion of the elongate body expands independently of the flexible member upon actuation of the actuator.

20. The apparatus of claim 19, wherein when the elongate body is in its expanded configuration, a volume of fluid disposed within the flexible member is greater than a volume of fluid disposed within the flexible member when the elongate body is in its collapsed configuration.

21. The apparatus of claim 19, wherein a distal end portion of the elongate body has an inner diameter when the elongate body is in its expanded configuration substantially corresponding to an outer diameter of a distal end portion of the flexible member when the flexible member is in its expanded configuration.

22. The apparatus of claim 19, wherein a first volume of fluid is disposed within the reservoir when the elongate body is in its expanded configuration, a second volume of fluid is disposed within the reservoir when the elongate body is in its collapsed configuration, the first volume of fluid being smaller than the second volume of fluid.

23. The apparatus of claim 19, further comprising:
a sheath coupled to the elongate body, the sheath configured to be percutaneously inserted at least partially into an interior of a vertebra when the elongate body is in its collapsed configuration and disposed within a lumen of the sheath, the actuator configured to move the sheath proximally while at least partially inserted into the vertebra such that the elongate body is moved from its collapsed configuration to its expanded configuration.

24. The apparatus of claim 19, wherein a distal end portion of the elongate body is formed with a nickel titanium alloy material.

25. The apparatus of claim 19, wherein the actuator includes a handle.

26. An apparatus, comprising:
an elongate body including a distal end portion defining a hollow interior region, the distal end portion having an expanded configuration and a collapsed configuration, the distal end portion including an end cap comprising a closed distal end, a plurality of arms extend from the end cap to the elongate body, each arm of the plurality of arms having a cutting portion, each cutting portion configured to disrupt tissue within a vertebra;
a flexible member having a distal end portion disposed within the interior region of the elongate body;
a reservoir coupled to the proximal end portion of the flexible member, a first volume of fluid being disposed within the reservoir when the elongate body is in its expanded configuration, a second volume of fluid being disposed within the reservoir when the elongate body is in its collapsed configuration, the first volume of fluid being smaller than the second volume of fluid; and
an actuator coupled to the elongate body and the flexible member and operable to independently control expansion of the distal end portion and the flexible member such that the distal end portion of the elongate body expands independently of the flexible member upon actuation of the actuator.

27. The apparatus of claim 26, wherein the flexible member has an expanded configuration and a collapsed configuration, the apparatus further comprising:
the actuator coupled to the reservoir, the actuator configured to actuate movement of the elongate body between its expanded configuration and its collapsed configuration while simultaneously actuating movement of the flexible member between its expanded configuration and its collapsed configuration.

28. The apparatus of claim 26, further comprising:
a sheath coupled to the elongate body, the sheath configured to be percutaneously inserted at least partially into an interior portion of a vertebra when the elongate body is in its collapsed configuration and disposed within a lumen of the sheath, the sheath configured to be moved proximally while at least partially inserted into the vertebra such that the elongate body moves from its collapsed configuration to its expanded configuration.

29. The apparatus of claim 26, wherein a distal end portion of the flexible member has an outer diameter when the flexible member is in its expanded configuration substantially corresponding to an inner diameter of a distal end portion of the elongate body when the elongate body is in its expanded configuration.

30. The apparatus of claim 26, wherein a distal end portion of the elongate body is formed with a nickel titanium alloy material.

31. The apparatus of claim 26, wherein when the elongate body is in its expanded configuration, a volume of fluid disposed within a distal end portion of the flexible member is greater than a volume of fluid disposed within the flexible member when the elongate body is in its collapsed configuration.

32. An apparatus, comprising: a sheath defining a lumen;
an elongate body disposed at least partially within the lumen of the sheath and including a distal end portion defining a hollow interior region, the distal end portion having an expanded configuration and a collapsed configuration, the distal end portion including an end cap comprising a closed distal end, a plurality of arms extend from the end cap to the elongate body, each arm of the plurality of arms having a cutting portion, each cutting portion configured to disrupt tissue within a vertebra;
an expandable member disposed at least partially within the lumen of the sheath and a distal end portion of the expandable member is disposed within the interior region of the elongate body; and
a reservoir in fluid communication with a proximal end portion of the expandable member, the sheath configured to be actuated between a first position in which the distal end portion of the elongate body is in the expanded configuration and the reservoir has a first volume of fluid and a second position in which the distal end portion of the elongate body is in the collapsed configuration and the reservoir has a second volume of fluid, an actuator coupled to the elongate body and the expandable member and operable to independently control expansion of the distal end portions of the elongate body and the expandable member such that the distal end portion of the elongate body expands independently of the flexible member distal end portion of the expandable member upon actuation of the actuator.

33. The apparatus of claim 32, wherein the sheath is configured to be percutaneously inserted at least partially into an interior portion of a vertebra when the distal end portion of the elongate body is in the collapsed configuration, the sheath configured to be actuated while at least partially inserted into the vertebra such that the distal end portion of the elongate body is moved from the collapsed configuration to the expanded configuration.

34. The apparatus of claim 32, wherein when the distal end portion of the elongate body is in the expanded configuration a volume of fluid disposed within the distal end portion of the expandable member is greater than a volume of fluid disposed within the distal end portion of the expandable member when the elongate body is in the collapsed configuration.

35. The apparatus of claim 32, wherein the distal end portion of the elongate body has an inner diameter when the distal end portion of the elongate body is in the expanded configuration substantially corresponding to an outer diameter of the distal end portion of the expandable member when the distal end portion of the expandable member is in an expanded configuration.

36. The apparatus of claim 32, further comprising:
a handle, the reservoir coupled to the handle, the handle configured to actuate the sheath between its first position and its second position.

37. A method, comprising:
disposing a distal end portion of a first elongate body at least partially into an interior portion of a vertebra while the first elongate body is in a collapsed configuration, the distal end portion defining a lumen, the distal end portion having a cutting portion and an end cap comprising a closed distal end, the distal end portion comprising a plurality of arm members that are fixed to the end cap;

expanding the first elongate body to an expanded configuration;

simultaneously with the expanding, moving a second elongate body disposed within the lumen of the first elongate body from a collapsed configuration to an expanded configuration such that the expanding of the first elongate body occurs independently of the moving of the second elongate body; and moving the first elongate body while the first elongate body is in the expanded configuration such that the cutting portion disrupts cancellous bone within the interior portion of the vertebra, the second elongate body configured to prevent at least a portion of disrupted cancellous bone from being disposed within the first elongate body during the moving.

38. The method of claim 37, wherein the expanding includes moving a volume of fluid from a reservoir to an interior portion of the second elongate body.

39. The method of claim 37, wherein the second elongate body is configured to prevent disrupted cancellous bone from entering into an interior portion defined by the plurality of arm members during the moving.

* * * * *